United States Patent [19]

Chamberlin et al.

[11] Patent Number: 4,775,943

[45] Date of Patent: Oct. 4, 1988

[54] METHOD AND APPARATUS FOR DETERMINING POLYMER MOLECULAR WEIGHT DISTRIBUTION PARAMETERS

[75] Inventors: Thomas A. Chamberlin; Hendrik E. Tuinstra, both of Midland, Mich.

[73] Assignee: The Dow Chemical Company, Midland, Mich.

[21] Appl. No.: 788,230

[22] Filed: Oct. 16, 1985

[51] Int. Cl.$^4$ .................. G01N 31/60; G01N 30/88; H01J 49/38; F25B 29/00

[52] U.S. Cl. .................. 364/497; 364/498; 73/61.1 C; 422/70

[58] Field of Search .................. 364/496–497, 364/510, 498, 499; 73/61.1 C, 861.41, 861.05; 210/565, 635, 656, 198.2; 422/70

[56] References Cited

U.S. PATENT DOCUMENTS

| | | | |
|---|---|---|---|
| 3,185,820 | 6/1966 | Williams et al. | 73/55 |
| 3,302,451 | 2/1967 | Martin | 73/61.1 C |
| 3,326,875 | 6/1967 | Moore | 73/61.1 C |
| 3,375,704 | 4/1968 | Thompson, Jr. et al. | 73/54 |
| 3,420,096 | 8/1968 | Hoyt | 73/54 |
| 3,458,437 | 7/1969 | Ouano | 73/61.1 C |
| 3,522,725 | 8/1970 | Waters | 73/61.1 |
| 3,535,917 | 10/1970 | Blair et al. | 73/61.1 C |
| 3,537,585 | 10/1970 | Waters | 210/198 |
| 3,581,773 | 10/1970 | Warren | 138/26 |
| 3,609,324 | 9/1971 | Machler et al. | 235/151.35 |
| 3,614,682 | 8/1971 | Smith | 235/151.12 |
| 3,649,200 | 3/1974 | Moore | 23/230 R |
| 3,674,373 | 2/1970 | Waters et al. | 23/61.1 C |
| 3,774,237 | 12/1973 | Hardway, Jr. | 324/61 |
| 3,808,877 | 5/1974 | Blair | 73/55 |
| 3,826,905 | 7/1974 | Valkama et al. | 235/151.12 |
| 3,837,217 | 9/1974 | Schutz | 73/61.1 C |
| 3,846,073 | 11/1970 | Baum et al. | 73/61.1 C |
| 3,924,448 | 12/1975 | Howard et al. | 73/55 |
| 3,930,399 | 1/1976 | Munk | 73/55 |
| 3,930,403 | 1/1976 | Cross et al. | 73/55 |
| 3,940,972 | 3/1976 | Norell et al. | 73/23.1 |
| 3,962,907 | 6/1976 | Peyronset et al. | 73/55 |
| 4,254,656 | 3/1981 | Sanford et al. | 73/61.1 C |
| 4,258,564 | 3/1981 | Hulme et al. | 73/61.1 C |
| 4,269,710 | 5/1981 | Hunt | 210/198.2 |
| 4,284,352 | 8/1981 | Carson et al. | 356/134 |
| 4,286,457 | 9/1981 | Johnson, Jr. | 73/53 |
| 4,299,253 | 11/1981 | Burton | 138/30 |
| 4,334,881 | 6/1982 | Reinert et al. | 23/230 |
| 4,335,616 | 2/1982 | Oliva et al. | 73/861.05 |
| 4,386,518 | 9/1982 | Zatko | 73/55 |
| 4,458,709 | 7/1984 | Springer | 137/10 |
| 4,468,742 | 8/1984 | Jenden et al. | 364/497 |
| 4,478,071 | 10/1984 | Lecacheux et al. | 73/55 |
| 4,482,966 | 11/1984 | Mito et al. | 364/498 |
| 4,491,024 | 1/1985 | Miller | 73/861.05 |
| 4,556,538 | 12/1985 | Mutsushita et al. | 422/70 |
| 4,578,990 | 4/1986 | Abbott et al. | 73/61.1 C |
| 4,598,765 | 7/1986 | Atwood et al. | 422/70 |
| 4,616,308 | 8/1986 | Morsheti et al. | 364/500 |
| 4,628,743 | 12/1986 | Miller, Jr. et al. | 73/861.05 |
| 4,674,323 | 6/1987 | Rulf et al. | 364/497 |

OTHER PUBLICATIONS

J. Polym. Sci., Part A, 2:835, (1964).
Yau, W. W. et al., Modern Size Exclusion Liquid Chromatography, John Wiley & Sons, New York, (1979), pp. 4, 126–138, 165–207, 294.
J. Poly. Sci., A-2, 8:1227, (1970).
J. Polym. Sci.—Symposium No. 43, (Ouano), pp. 299–310, (1973).
Ouano et al., J. Poly. Sci., 12:307–322, (1974).
Callec, G. et al., J. Poly. Sci., 22:287:293, (1984).
Chamberlin, T. A. et al., Anal. Chem., 55:428–432, (1983).

(List continued on next page.)

Primary Examiner—Parshotam S. Lall
Assistant Examiner—Ellis Ramirez
Attorney, Agent, or Firm—Saidman, Sterne, Kessler & Goldstein

[57] ABSTRACT

Method and apparatus for determining various molecular weight distribution parameters by concurrent measurement of hydrodynamic volume, specific viscosity and mass. Essentially concurrent viscosity and mass detectors are described, as are improved methods for viscosity detection, which together provide substantially improved results.

42 Claims, 14 Drawing Sheets

OTHER PUBLICATIONS

Moore, J. C.—"Gel Permeation Chromatography", Nat. Acad. of Science, Washington, D.C., 1968, pp. 273–284.

Tung, L. H. et al.—3 Appl. Poly. Sci., 10:1261, (1966).

Letot, L., et al., J. Liq. Chrom., 3:427, (1980).

Abbott, S. D. et al., ACS, 178, Mtg. Abst., Anal-79, (1979).

Hamielec, A. E., J. Liq. Chrom., 3:381, (1980).

Miller, T. E. et al., Anal. Chem., 54:907–910, (1982).

Ambler et al., J. Polym. Sci., Poly Chem., 12:1759, (1974).

Zimm et al., J. Chem. Phys., 17:1301, (1949).

Kamath et al., J. Polym. Sci., A–1, 5, 2023–2030, (1967).

FACSS Mtg. Schedule.

Abstract, Lesec et al., Analusis, 1976, 4(10), 456–62.

Lecacheux et al., Polymer Preprints, 23, #2, (126–127), 1982.

Malihi et al., ACS Org. Coatings, (1983), 760–764.

Koehler et al., ACS, Org. Coatings/Applied Proc., 48, 617–621, (1983).

Malihi et al., Abstract, 806, (Pittsburgh Conf., 1982).

Letot et al., Journal of Liq. Chrom., 3(11), pp. 1637–1655, (1980).

Lecacheux et al., J. Liq. Chrom., 5(2), 217–228, (1982).

Lecacheux et al., J. Liq. Chrom., 5(12), 2227–2239, (1982).

Hoffman et al., Anal. Chem., 56, 9, 1682–1685, (1984).

Miller et al., Amer. Lab., Jan. 1983, (reprint).

METHOD AND APPARATUS FOR DETERMINING POLYMER MOLECULAR WEIGHT DISTRIBUTION PARAMETERS

BACKGROUND OF THE INVENTION

1. Field of the Invention

The invention to which this application is directed concerns method and apparatus for determining polymer molecular weight distribution (MWD) measurements using a "Benoit" or universal approach. In the practice of this invention, the concurrent measurement of polymer mass and solution viscosity of a stream eluting from a typical size-exclusion chromatographic experiment generates data. This data, in combination with data relating to hydrodynamic volume, is evaluated by a sophisticated computer program (software). Values for MWD parameters are produced which are in complete agreement with results generated using low angle laser light scattering techniques (LALLS). Specific characteristics of the invention system, i.e. close-coupling of the mass and solution viscosity detectors and data manipulation which eliminates the requirement for highly sensitive viscosity detection, allows the measurement of correct molecular weight distribution and certain solution properties for any soluble polymer without prior knowledge of the nature or structure of the polymer.

BRIEF DESCRIPTION OF BACKGROUND ART

Measurement of the molecular weight distribution of high molecular weight polymers is of particular interest because the physical properties of the polymers are related thereto. During the course of a polymerization reaction, a large quantity of polymer chains are initiated, grow, and then are terminated. The number and length (or weight) of the polymeric chains formed during the reaction vary with the reaction mechanism and the reaction conditions employed. At times, the distribution of these chains is accurately predictable from statistical considerations; at other times (for example, non-equilibrium processes), a priori predictions are not accurate.

In order to properly evaluate the molecular weight distribution parameters of a given polymer, it is necessary to separate solutions of polymeric materials on the basis of molecular size. Size-exclusion chromatography (SEC) is a liquid column chromatographic technique which sorts molecules according to their size. The sample solution is introduced into a column which is filled with a rigid-structure, porous-particle column packing, and is carried by solvent through the column. The size sorting takes place by repeated exchanges of the solute molecules between the bulk solvent of the mobile phase and the stagnant liquid phase within the pores of the packing. The pore size of the packing particles determines molecular size range within which separation occurs. Modern high-performance size-exclusion chromatography (HPSEC) has resulted from the development of small, more rigid porous particles for column packings and permits separations to be made much faster and with much greater resolution. One aspect of SEC is gel permeation chromatography (GPC), first demonstrated by J. C. Moore of the Dow Chemical Company in 1964. Moore disclosed the use of cross-linked polystyrene "gels" for separating synthetic polymers soluble in organic solvents (*J. Polym. Sci.*, Part A, 2: 835 (1964)). Today GPC normally is used as an analytical procedure for separating molecules by their difference in size and to obtain molecular weight averages or information on the molecular weight distribution of polymers. It may, however, also be used for preparing various molecular weight fractions for further use. A concentration-sensitive differential refractometer may be used to generate a curve which relates relative size distribution to weight concentration. With proper calibration, the raw data may be converted to a molecular weight distribution curve and the respective molecular weight averages may be calculated. See Yau, W. W. et al., *Modern Size Exclusion Liquid Chromatography*, p. 4, John Wiley & Sons, New York (1979).

In GPC, when the packing is flushed by a suitable solvent, an exchange process takes place. This process begins with the largest polymer being eluted first and continues in sequence until all of the polymer has been removed, ending with the smallest polymer being eluted. An accurate detection of the amount and molecular weight of fractions of the effluent from the chromatograph would make possible a determination of the molecular weight distribution of a polymer mixture. One technique used in the prior art for measuring the molecular weight distribution employed two detectors, a differential refractometer to measure mass, and a volume counter to measure elution volume. Using suitable correlations, these two measurements were translated into mass of effluent polymer and the molecular weight. However, the measurement of molecular weight by counting the volume eluted may be done only by first obtaining information as to the molecular weight of the polymer leaving the packed column after a certain amount of solvent has passed through. By using polymer fractions of narrow and known molecular weight, it is possible to prepare a calibration curve which will permit the translation of volume of solvent effluent into molecular weight. Such a procedure is complicated, time-consuming, and is applicable only in the rare instances when standard polymers are available. Unknown polymers cannot be satisfactorily analyzed using this technique. Further, while a differential refractometer does measure mass directly, this technique requires the assumption of linear proportionality between mass and refractive index and also requires the assumption that the polymer has a constant refractive index over a wide range of molecular weight and structure.

A more recent development, reported in the *J. Poly. Sci.*, A-2, 8: 1227 (1970), is based on the finding that the hydrodynamic volume of a polymer is a means of correlating the elution behavior of most polymers. A single universal correlation curve may be developed from known polymers and thereafter be applied to other polymers separated in the same column. In this manner, hydrodynamic volume may be related to the product of intrinsic viscosity and molecular weight so that by measuring intrinsic viscosity, molecular weight may be determined. Intrinsic viscosity is determined as the natural log of the ratio of the viscosity of the polymer solution to that of the solvent divided by the polymer concentration (i.e., the relative viscosity divided by the concentration), extrapolated to zero concentration. By means of the universal curve, no prior knowledge of the polymer composition over a wide variety of polymers is required.

In U.S. Pat. No. 3,837,217 to Schulz, there is disclosed a method for measuring molecular weight distribution. A polymer is separated into fractions by hydrodynamic volume within a gel permeation chromatographic column by passage of a solvent through the chromatographic column, so that the polymer is removed in a sequence determined by molecular size. The eluted polymer solution is separated into fractions of equal volume and the viscosity of each fraction is measured, along with the concentration of each fraction. From this data, the intrinsic viscosity of each fraction is calculated and the universal correlation between molecular weight and intrinsic viscosity applied to obtain molecular weights characterizing each fraction. The mass of the polymer corresponding to each fraction is measured directly by evaporating a sample of solution on a piezoelectric crystal and weighing the polymer residue by the change in vibrational frequency of the crystal. In the Schulz disclosure, volume is determined by use of a syphon, the syphon forwarding a fixed volume (5 ml.) to the automatic viscometer. Viscosity is measured by the flow time required for each fraction to pass through a capillary tube.

Ouano, A. C., *J. Polym. Sci.*, Symposium No. 43, 299–310 (1973), disclosed a method and apparatus for determining absolute molecular weight distribution of polymers using only polystyrene calibration standards. GPC-fractionated polymer was passed through a detector system comprising a pressure cell and capillary viscometer, a constant flow rate pumping system, a concentration detector, and a computer interfacing system. The detector system provided two chromatograms, the first a correlation of pressure drop against retention volume and the second a correlation of concentration against retention volume. The viscometer disclosed by Ouano was based on the measurement of effluent pressure drop through a capillary to give a continuous trace of the change in viscosity of GPC effluents as a function of retention volume. Ouano recognized the limitation of the viscosity measurement system in being dependent upon very precise flow rate and very sensitive pressure transducers. Ouano did recognize that in order for the viscometer system to be sensitive to very small pressure changes, high sensitivity and small mixing volume for the viscometer system were required, and suggested a mixing volume of less than 10 ul for the viscometer.

Ouano et al., *J. Poly. Sci.*, 12: 307–322 (1974), proposed a molecular weight detector system which described in greater detail the previously-mentioned Ouano system. In the system disclosed by Ouano et al., relative viscosity was required to be measured with an accuracy to at least three decimal places and the time lag between the pressure transducer detector and the concentration detector was required to be less than one second $$\left(\text{example: } 1 \text{ sec} \times \frac{\text{min}}{60 \text{ sec}} \times \frac{1 \text{ ml}}{\text{min}} = 20 \text{ul}\right).$$

The viscometer and mass detector, two separate instruments, were thermostated at 23° C. with the polymer solution flowing through the mass detector prior to flowing through the viscometer. In addition to the inherent disadvantages provided by a system requiring measurements of relative viscosity to at least three decimal places and a maximum of a one second time lag between the measurement made by the pressure transducer detector and the concentration detector, where each detector is a separate unit, the Ouano et al. system has the further disadvantage that back pressure generated by the viscometer creates inaccuracy in mass measurement. The Ouano et al. system also requires a highly sophisticated temperature control mechanism.

Callec, G. et al., *J. Poly. Sci.*, 22: 287–293 (1984), also disclose a system for determining MWD, this time for polymers which are insoluble in conventional common GPC solvents. The Callec et al. system utilizes strongly alkaline solutions as eluent and polystyrene sulfonates, polyethylene glycols, and dextrans as secondary calibrants. Continuous monitoring of intrinsic viscosity resulted from coupling a visco-detector with a classical differential refractometer. The Callec et al. system would appear to be a step backward in the progression of the technology in that Callec et al. appear to fail to appreciate the significance of highly specific temperature control. Further, the visco-detector cell volume is in the range of 62 ul.

Lacacheux et al., U.S. Pat. No. 4,478,071, disclose a viscometer adapted to operate continuously to be associated with a GPC device for detecting molecular weight distribution proportional to hydrodynamic volume of the macromolecules in solution. The suggested system would include both a concentration detector and a viscometer, the latter comprising means for measuring loss of pressure across a capillary, the capillary consisting of a tube having a length of several meters, would about itself according to a helix, having a diameter of at least 10 cm. The internal diameter of the capillary is disclosed as being between 0.2 and 0.3 mm, necessitating a capillary volume of somewhere in the range of several hundred microliters. According to Lacacheux et al., the large helix diameter of the capillary is required in order to negate the effect of centrifugal force, the centrifugal force introducing error into the measurement of differential pressure.

Chamberlin, T. A. et al., *Anal. Chem.*, 55: 428–432 (1983), disclose the use of a thermal pulse time-of-flight flow meter for measuring elution volume in size-exclusion chromatography and emphasize the criticality of accurate elution volume measurement for the purpose of accurate molecular weight distribution determinations. Recognizing that the accuracy of calculated molecular weight at any particular elution volume is about 10–20 times the precision of the corresponding volume measurement, coupled with the fact that modern columns generally possess active volumes in the range of 2–5 ml, Chamberlin et al. concluded that a precision in derived molecular weight of 5% would require at least 0.5% precision in elution volume measurement, i.e. reproducibility to within 10–25 ul. Based on their experimental work, Chamberlin et al. concluded that the thermal pulse time-of-flight device represents an improvement upon prior art techniques which require highly sophisticated pumping systems, syphon dump counters, direct weighing, internal standards, and the like.

Waters, U.S. Pat. No. 3,522,725, discloses a liquid chromatograph utilizing a small volume chromatography column and a refractometer cell housed in a single heat exchanger so that the coupling distance between them is kept to a minimum. The temperature of the liquid being analyzed is kept constant by circulating it through a heat exchanger just before it enters the column. By minimizing the coupling distance between the column and the cell, the temperature of the sample remains substantially the same from the time it enters the column until it leaves the cell. Consequently, the refractive index of the sample liquid remain constant as well. As a result, each component of the sample elutes properly from the column and the index of refraction of each component is accurately reflected in the output of the refractometer. Further, by minimizing the coupling distance between the column and the cell, there is a minimum dead volume in the system so that there is minimum zone mixing. This minimal zone mixing permits the generation of a very discriminating electrical output in the form of sharp, narrow peaks.

Based on the accumulation of background materials described above, it may be seen that the determination of MWD by use of the Benoit or universal technique, while presenting exciting possibilities, is fraught with difficulty. Extreme sensitivity of the system to temperature differential (Waters, supra), high sensitivity requirements in the instrument for determining pressure differential (Ouano, supra) and elution volume (Chamberlin et al., supra), as well as error introduced by peak band spreading as a result of zone mixing of fractions (Waters, supra), have served as impediments to the development of a method and apparatus which is simple to operate and which provides highly accurate MWD vectors. The present invention represents a substantial advance and overcomes the problems of previous systems.

SUMMARY OF THE INVENTION

Recognizing the need for the development of a fast, accurate and general technique for MWD measurements, the inventors began exploring the possibility of using the Benoit or universal technique for molecular weight distribution measurement, placing emphasis on development of an effective replacement of the involved and expensive SEC-LALLS analysis technique. A more appropriate analysis would be one that was reasonably accurate (±10% of the "truth") and which could be easily and quickly carried out by someone of modest chromatographic experience. Ideally, the method and apparatus would produce MWD parameters which were absolute values rather than being mere calibration equivalent values. Further, as contemplated, the method and apparatus would provide Mark-Houwink coefficients, whole sample intrinsic viscosity, branching information and a variety of other MWD vectors.

With these ends in mind, the inventors have developed a method and apparatus for progressively, concurrently measuring polymer mass and solution viscosity for a stream eluting from a typical GPC experiment and correlating the data generated by the concurrent measurement of polymer mass and solution viscosity with hydrodynamic volume data of the polymer mass by means of elution volume. In addition, the present inventors have developed both the theory and appropriate software to reduce the data which is collected to various molecular weight distribution parameters of the polymer under examination.

The method of the present invention comprises fractionating a solution of the polymer sample to be analyzed by size-exclusion chromatography to produce a progressive stream of polymer solution sorted by polymer hydrodynamic volume, progressively measuring the capillary pressure drop of said polymer solution, and progressively measuring the concentration of said polymer solution fractions by means of a mass detector to produce a succession of concentration values, progressively determining the specific viscosity of said polymer solution fractions using the change in capillary pressure drop from a known electronically adjusted value for the solvent, wherein said capillary pressure drop measurements and mass detector measurements are in close-coupled proximity and are in a thermal sink, progressively measuring the elution volume of said polymer solution fractions to produce a succession of elution volume values, determining said hydrodynamic volume of each of said polymer sample fractions as a function of said elution volume values, and correlating said specific viscosity values, said concentration values, and said hydrodynamic volume values by use of said elution volume measurement to determine molecular weight vectors or moments of the polymer sample.

The apparatus of the present invention comprises a size-exclusion chromatography column, a means for determining capillary pressure drop measurements, a means for determining mass, and a means for determining elution volume, said means for determining capillary drop and said means for determining mass positioned in close-coupled proximity and in a thermal sink.

A further aspect of the present invention includes a technique for compensation of a value representing pressure drop across the capillary which avoids the requirement of excessive dynamic range for analog-to-digital converters used.

DESCRIPTION OF THE PREFERRED EMBODIMENTS

I. The Apparatus

The measurement of the molecular weight of polymers using size-exclusion chromatography (gel permeation chromatography) may be made absolute if a concurrent measurement of the intrinsic viscosity ($[n]$) is carried out since the SEC experiment separates the various polymer molecules according to their hydrodynamic volume in solution. The hydrodynamic volume is determined by the molecular weight and the properties of the solvent being used in the experiment. The relationship which describes this property (hydrodynamic volume) is shown below:

Hydrodynamic Volume = $[n] \times$ MW (molecular weight).

The hydrodynamic volume of any particular sample of eluting polymer is determined by its unique elution volume ($V_e$). The measurement of $[n]$ is accomplished by concurrently measuring both the polymer concentration (C) and the corresponding solution specific viscosity $n_{sp}$. These latter two values are then converted into $[n]$ via the well-known relationship:

$$[n] = n_{sp}/C$$

$$[n] = \lim_{C \to o} \frac{n_{sp}}{C}$$

Concentration may be readily measured using conventional mass detectors such as a differential refractive index detector.

By measuring the small changes in a signal from a differential pressure transducer placed across a short length of capillary tubing, under conditions of constant flow, it is possible to measure $n_{sp}$. Under conditions of constant flow, changes in output from the transducer may be related to changes in solution viscosity via the equation shown below:

$$\Delta P = Q \cdot n_{sp} \cdot G \cdot \text{Flow Rate}$$

where $\Delta P$ is the observed pressure drop, Q and G are constants related to the geometry of the capillary and to the instrument used to measure the pressure. By suitable manipulation of the above equation, it is possible to arrive at a value for the solution specific viscosity which is used to determine the polymer intrinsic viscosity ($[n]$).

Thus, it may be seen that determination of molecular weight distribution depends upon the precise measurement of three properties of the eluting stream from the SEC experiment. The three precise measurements required are:

(1) the elution volume ($V_e$);
(2) the polymer concentration (C); and
(3) the specific viscosity ($n_{sp}$).

A. THE SYSTEM

Figure 1:
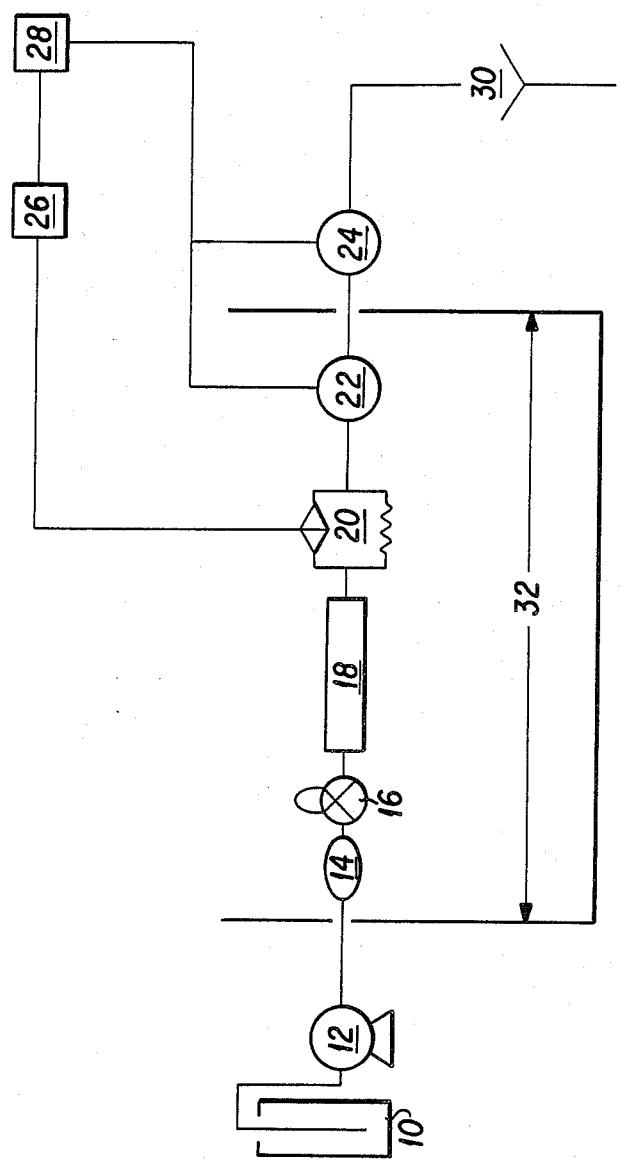
FIG. 1 is a schematic drawing of the component parts of the system represented in block form.

FIG. 1 is a schematic drawing of the component parts of the system represented in block form. Referring to FIG. 1, the reference numeral 10 is a solvent reservoir, 12 is a conventional high pressure liquid chromatography (HPLC) pump, 14 is a damping system, 16 is a sample injection valve, 18 is a size-exclusion column (gel permeation chromatography column), 20 is a viscosity detector, 22 is a mass detector, 24 is an elution volume detector, 26 is an electronic signal compensation device (detailed in connection with FIG. 5 below), 28 is a data collection system, 30 is a collector, and 32 is a temperature control system.

In practice, solvent from solvent reservoir 10 is introduced into the system through HPLC pump 12 and passes through damping system 14 prior to entry into the size-exclusion column 18. Exiting size-exclusion column 18, the solvent then passes through viscosity detector 20, mass detector 22, and elution volume detector 24 prior to discharge from the system. At this point, with only solvent flowing through the system, the viscosity detector 20 and mass detector 22 are calibrated or "zeroed." Once the system has been calibrated and stabilized, the particular polymer sample to be analyzed is introduced into the system through injection valve 16 and then passes into the size-exclusion column 18. In size-exclusion column 18, the polymer sample is fractionated according to hydrodynamic volume, the largest molecules exiting the column first and the smallest molecules exiting the column last. The fractionated sample then passes successively through the viscosity detector 20, mass detector 22, and elution volume detector 24, each of detectors 20, 22 and 24 generating a signal which passes to data collection unit 28. The eluted fractions then pass out of the system into container 30.

B. MOBILE PHASE (SOLVENT) RESERVOIRS

Since flow rates in gel permeation chromatography are typically 1–3 mls. per minute, and separations usually are completed in a half-hour or less, the volume of mobile phase used for a single analysis is relatively small. Reservoirs are preferably made of stainless steel or glass, but should be inert to the mobile phase and not easily broken. Where required, the mobile phase may be degassed in situ to prevent bubbles from forming in the detector during separation. The reservoirs can be equipped with a heater, a stirring mechanism, and separate inlets for vacuum or nitrogen purge to facilitate in situ degassing. Mobile phase reservoirs are described in detail in Yau et al. (supra), pages 126 to 128, incorporated by reference herein.

C. THE HPLC PUMP

The pump, also known as the solvent-metering system, must provide a constant, reproducible supply of mobile phase to the column. Relatively high pump pressures are required to overcome resistance to flow offered by the small particles used in the columns. The solvent-metering or pumping system can often be the limiting factor for accurately determining the performance of the chromatographic separation, particularly when molecular weight information is desired. Constancy of flow rate is especially important with other factors such as pump resettability, short-term precision, pump pulsation or "noise," drift, and flow rate accuracy also being of significance in pump determination.

Any of the pumps conventionally used in HPLC are considered to be equivalent for the purposes of this invention. Typically, the pump is of the reciprocating, positive-displacement, or constant-pressure type. A good discussion of HPLC pumps appears at pages 128-138 of Yau et al., supra, incorporated by reference herein. Typical pumps include the LDC Constametric III pump, produced by Laboratory Data Control Division of Milton Roy, and Waters Model 45LC or 6000A, produced by Waters Associates, Division of Millipore, with the LDC Constametric III pump preferred.

D. PUMP "NOISE" OR PULSATION DAMPING MECHANISMS

Pump "noise" or pulsation results from flow changes, a function of operational aspects of the pumping mechanism such as piston movement and check valve operation. Accordingly, it is preferred that the system include a pulse damping device or system as well. Suitable damping systems are well-known and conventionally used in gel permeation chromatography; all those systems commonly in use are considered to be equivalents for the purposes of this invention.

Figure 2:
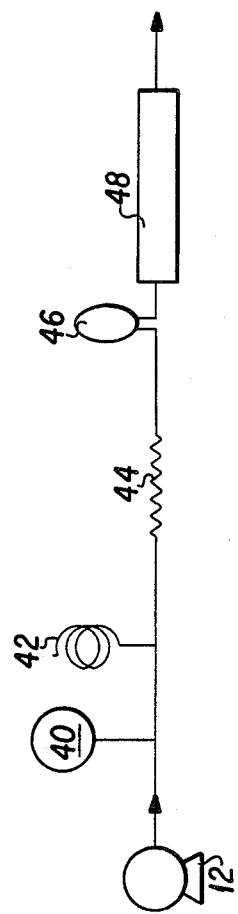
FIG. 2 is a schematic representation, in block diagram form, showing a suitable damping system.

FIG. 2 is a schematic representation, in block diagram form, showing a suitable damping system. In FIG. 2, reference numeral 12 is the HPLC pump, 40 is a pressure gauge, 42 is flattened one-quarter inch stainless steel tubing, 44 is capillary tubing, 46 is a high sensitivity filter, and 48 is a gel permeation chromatography column used for flow smoothing. A typical example of stainless steel tubing 42 is made by Handy & Harmon, Morristown, Pa., under the product name Lichrom-A-Damp II. In one embodiment, an LDC Mark III followed by a Lichrom-A-Damp II are used to minimize the flow noises created by the pump.

This particular arrangement routinely results in flow noise of approximately 0.15 mv out of a total signal of 500 mv (less than 0.05%).

E. THE SAMPLE INJECTION VALVE

The method of introducing the sample into the column can be a significant factor in determining column chromatography performance. The sample should be introduced into the column in a sufficiently narrow band so that peak broadening from this cause is negligible. Ideally, the sample injector should introduce sharp plugs of a wide variety of samples into the columns with insignificant band broadening. Injectors should be convenient to use, reproducible, and operable against high back pressures. Additionally, in some instances, it is required to inject samples at elevated temperatures to meet solubility requirements.

One sampling device of particular utility in the present invention is the microsampling injector valve. These special valves permit the sample to be introduced reproducibly into pressurized columns without significant interruption of solvent flow, even at higher temperatures. The typical injection valve is the Rheodyne 7125, 100 ul loop, made by Rheodyne, Inc., Cotati, Calif.

F. THE SIZE-EXCLUSION COLUMNS (GEL PERMEATION CHROMATOGRAPHY COLUMNS)

The separation of polymer molecules in solution by means of porous material is now generally referred to as gel permeation chromatography. This technique has become widely accepted as a method of analyzing polymers by separating said polymers into fractions by molecular size. Using well-characterized narrow fractions of a polymer as samples, a column may be calibrated in terms of its separating and band-spreading characteristics by known methods. A "universal" calibration results when molecular size is expressed as hydrodynamic volume, that is, as the product of molecular weight and intrinsic viscosity. The molecular weight distribution of an unknown sample of a given polymer may then be obtained by finding that distribution which, when subjected to the known separating and band-spreading characteristics of the particular column, would have given the chromatogram. This method is further discussed by Moore, J. C. in *Characterization of Macromolecular Structure*, Publication 1573, Nat. Acad. of Science, Washington, D.C., 1968, pp. 273-284, and Tung, L. H. et al., *J. Appl. Poly. Sci.*, 10: 1261 (1966), both incorporated by reference herein.

The separation takes place in a chromatographic column filled with particles of a rigid, porous "gel," highly cross-linked porous polystyrene and porous glass being preferred column-packing materials. The pores of these gels are the same size as the dimensions of the polymer molecules. As the dissolved polymer molecules flow past the porous beads, they diffuse into the internal pore structure of the gel to an extent depending on their size and the pore-size distribution of the gel. Larger molecules can enter only a small fraction of the internal portion of the gel, or are completely excluded; smaller polymer molecules penetrate a larger fraction of the interior of the gel. Accordingly, the larger molecules spend less time inside the gel and flow through the column fastest. The different molecular species are eluted from the column in order of their molecular size, with the largest emerging first. For the purposes of the present invention, any of the conventional and well-known columns and packing materials are considered to be equivalents. Yau et al., supra, at pages 165-207, includes a complete discussion of columns, column packing materials, column packing techniques, column dimensions, and column configurations. Yau et al. is incorporated by reference herein.

Typical columns include gel permeation chromatography columns made by Du Pont, Wilmington, Del., under Model Nos. PSM-1000 and PSM-60.

G. THE VISCOSITY DETECTOR (VDP)

As described above, the method and apparatus of the present invention require the concurrent measurement of hydrodyanmic volume, mass and specific viscosity for the determination of molecular weight distribution parameters. The following brief derivation is designed to set out the performance criteria for a suitable viscosity detector.

For laminar flow through a capillary, the pressure drop ($\Delta P$), is given by the Poisseuille relationship:

$$\Delta P = fQ(n)$$

Where f is the flow rate, Q is a collection of geometric factors, and n is the viscosity of the solution passing through the capillary.

The specific viscosity ($n_{sp}$) of any solution is defined as follows:

$$n_{sp} = (n_{solution} - n_{solvent})/n_{solvent}$$

Capillary pressure drop $\Delta P$ being a function of viscosity, this equation may also be written as:

$$n_{sp} = (\Delta P_{solution} - \Delta P_{solvent})/\Delta P_{solvent}$$

assuming constant flow.

The viscosity (or capillary pressure drop) of a solvent containing polymers is considered to be the viscosity of the solvent plus the contribution to viscosity due to the polymer ($d\Delta P_{polymer}$). This leads to the relationship shown below:

$$\Delta P_{solution} = \Delta P_{solvent} + d\Delta P_{polymer}$$

$$n_{sp} = (\Delta P_{solvent} + d\Delta P_{polymer} - \Delta P_{solvent})/\Delta P_{solvent}$$

$$n_{sp} = d\Delta P_{polymer}/\Delta P_{solvent}$$

From this last equation, it is apparent that if the pressure drop for the solvent is known, then it is only necessary to measure the change from this value in order to determine the specific viscosity of any solution passing through the capillary. This leads to the equation:

$$n_{sp} = d\Delta P_{polymer}/\Delta P_{solvent} = d\Delta V_{polymer}/\Delta V_{solvent}$$

where $\Delta V$ is the voltage output from a suitable transducer system.

Assume that, in a given experiment, 50 ugm of polymer will be eluted in 20 ul of solution. These are not unreasonable conditions for a high performance GPC experiment using low dispersity polymers. This represents an average concentration of 0.25 gm/dl. If the molecular weight of the polymer is taken to be 100,000, with attendant Mark-Houwink coefficient K of $50 \times 10^{-5}$ gm/dl and 0.50 for the exponent (a) in the equation:

$$[n] = K(MW)^a$$

there would result a predicted intrinsic viscosity [n] of 0.16.

For the dilute conditions being discussed, the intrinsic viscosity will be determined by the ratio of the specific viscosity and the concentration according to the formula:

$$[n] = n_{sp}/C$$

This leads to a predicted specific viscosity for such a collection of conditions on the order of 0.04.

The ratio of solution and solvent signals from the detector must then also be on this order. A reasonable range of expected signal ratios might be 0.002–0.200. For adequate sensitivity, a signal-to-noise ratio of 10 might be desired. This leads to the requirement for noise in the system on the order of ±0.02%. The preceding development predicts that for a sample of 50 ugm of polymer (molecular weight (MW)=100,000; [n]=0.16) eluting in 20 ul, a signal change equal to about 4% of that detected in connection with the pure solvent will be generated.

Figure 3:
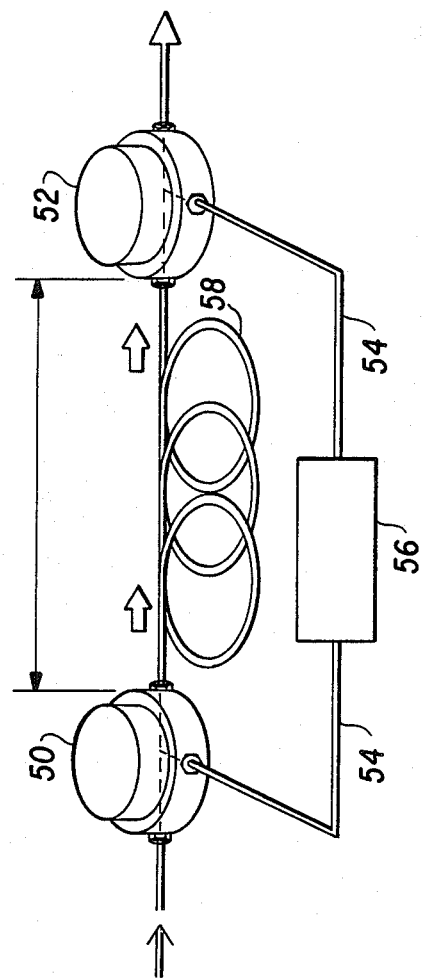
FIG. 3 is a representational drawing of a capillary configuration suitable for producing a differential pressure viscometer for this invention.

Determination of specific viscosity by determination of pressure drop across a short capillary has been well reported in the literature. See Ouano, A. C., *J. Poly. Sci., Symp.* 43, 299 (1973); Letot, L. et al., *J. Liq. Chrom.*, 3: 427 (1980); Abbott, S. D. et al., *ACS*, 178, *Mtg. Abst.*, Anal-79 (1979); Hamielec, A. E., *J. Liq. Chrom.*, 3: 381 (1980); and Ouano, A. C. et al., *J. Poly. Sci., Chem.*, 12: 307 (1974), all incorporated by reference herein. The technique for obtaining the viscosity of some eluting solution requires the measurement of the pressure drop across a capillary in the system under conditions of constant flow. One capillary which is found to be eminently suitable is available from Supelco, Inc. of Bellefonte, Pa. This device, pictured in FIG. 3, consists of two zero dead volume "T" connectors, a short length (about 20 cm.) of 0.006 inch ID by 1/16 inch OD stainless tubing, and the necessary fittings for plumbing into a GPC system. The volume of the capillary (which is the detector for this system) is approximately 3.5 ul). In practice, the unit is connected directly to the exit from the GPC portion of the system. The eluting stream is forced to traverse the capillary on the way to the remainder of the detector system. The other two outlets are led to the appropriate sides of a differential pressure transducer, typically a Validyne DP15 transducer (Validyne Engineering Corp., Northridge, Calif.). Tubing of 0.01 inch ID is used for these lines. Referring to FIG. 3, reference numerals 50 and 52 are zero dead volume "Tee" connectors, 54 is the line to the differential pressure transducer, 56 is the differential pressure transducer and 58 is the capillary.

The transducers are operated in the wet/wet mode by carefully filling the lines and cavities with solvent. The transducer is activated and a corresponding signal is generated using a Validyne CD-101 carrier demodulator or its equivalent. A signal from this system is voltage-divided to some desired value (usually 200–1,000 mv)-and then bucked to zero. In this way, it is possible to arrange the system so that a flow of 1.0 ml/min. (nominal) will produce a 500 mv. output from the transducer, while the recording system monitors changes in the signal level of 10 mv. (2% full scale). The circuit used is discussed below in connection with FIG. 5.

For systems maintaining constant flow, changes in the differential pressure are directly related to changes in the viscosity of the sample generating the differential pressure. For a typical case (i.e. sensitivity ±2% full scale), a polymer solution with a specific viscosity of 0.004 would generate a 20% (2.0 mv.) reading on the data collection system.

H. THE CONCENTRATION DETECTOR

The mass detector 22 of FIG. 1 may be any suitable device such as a photoelectric colorimeter or a refractometer, for measuring relative changes in the concentration of the solution effected by the separation column. A differential refractometer (DRI) represents one embodiment for use in the present invention and comprises a combination of optical, mechanical and electrical components. Differential refractometers are probably the most widely used detectors for use in gel permeation chromatography analyses. The device continuously measures the difference in refractive index between the mobile phase and the mobile phase containing the sample. Differential refractometers are described in greater depth in Yau et al., supra, pages 148–156; U.S. Pat. No. 3,458,437 to Ouano; and U.S. Pat. No. 3,674,373 to Waters et al., all incorporated by reference herein.

I. THE DUAL DETECTOR OF THIS INVENTION

The concurrent measurement of specific viscosity and polymer concentration in a stream eluting from a typical SEC experiment is influenced by at least three factors. One of these is temperature variation during the viscosity measurement, another is incorrect accommodation of the volumetric offset (the volume in the transmission line connecting the two devices) between the two detectors, while the third is sample dilution during transport between the two detectors. One aspect of the present invention, said aspect achieving a minimization of these three factors, is the direct incorporation of the capillary through which pressure drop is measured by the mass detector.

FIG. 4 represents a schematic of the development of the dual detector. The starting point for the development of the dual detector was a differential refractometer made by Waters Associates, Inc., Framingham, Mass., Model 401. FIG. 4A represents the unmodified model 401 refractometer. This detector was completely dismantled and the solder melted from the channel leading the two inlet lines to the bottom of the detector stage. FIG. 4A shows the original detector, including the original plumbing channel.

Figure 4A:
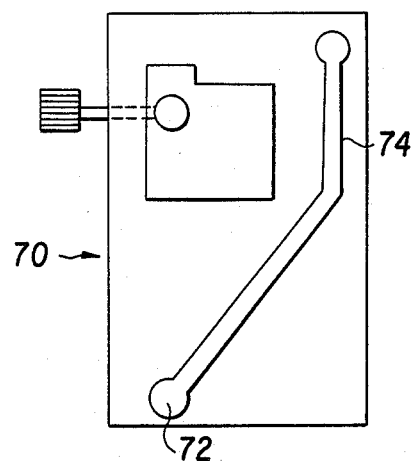
FIGS. 4(a) through 4(d) are schematic drawing representing the development of the dual detector of this invention.
Figure 4B:
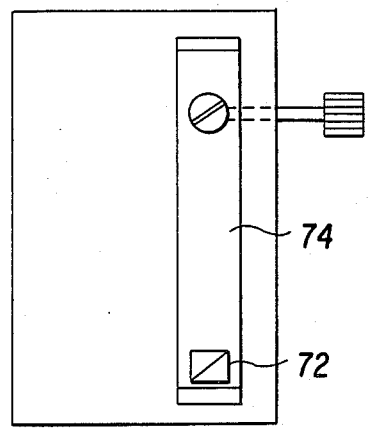
Figure 4C:
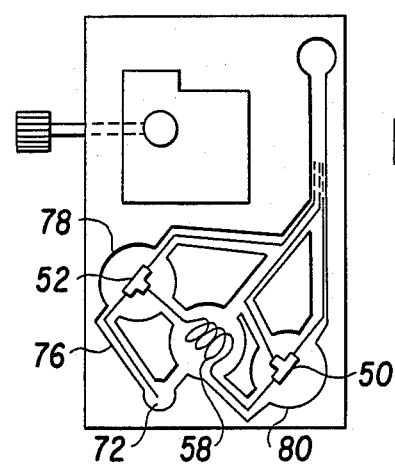
Figure 4D:
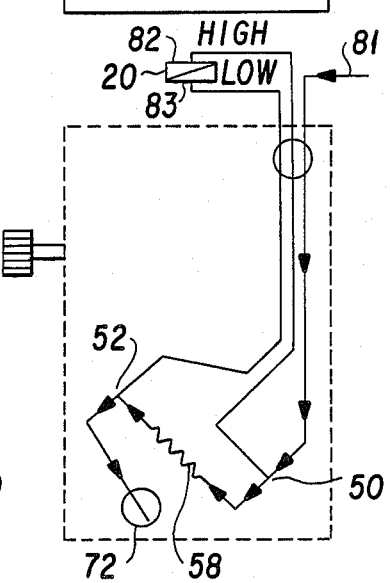

The model 401 refractometer, as will be understood by those skilled in the art, comprises an aluminum block housing a two-chamber differential refractometer cell; one of the chambers contains a reference sample and the other a sample under analysis. By analysis of the refraction of light through the two, one can compare the refractive indices of the two solutions, thus obtaining an indication of variations in concentration in the sample chamber. The large block of aluminum is used primarily for thermal mass so as to stabilize the temperature of the two solutions. FIG. 4A shows the bottom view of the Waters Model 401 detector, and FIG. 4B shows a top view of the Waters detector. The DRI cell is shown at the bottom at 72 and a channel 74 connects the inlet to the detector cell 72. According to one aspect of the invention, additional channels were milled as shown generally at 76 in FIG. 4C. The capillary 58 shown in FIG. 3 and again in FIG. 4C at 58 was inserted in one of the channels, while the zero dead volume tee fittings 50 and 52 were inserted in chambers 80 and 78, respectively. The differential pressure transducer 20 was added externally of the aluminum block, as shown schematically in FIG. 4D, which shows the plumbing of the dual detector of the invention. Thus, fluid to be sampled is inlet at 81, is passed by way of the first tee 50 to the high side 82 of the differential pressure transducer 20, which, as mentioned, is a Validyne Corp. Model DP15. Fluid is also directed from the zero dead volume tee 50 to the capillary 58. Input to the low side 83 of the differential pressure transducer is from the other side of the capillary 58, taken from the second tee 52. Finally, the sample exits the viscosity detector just described and enters the cell of the differential refractometer shown at 72, thence to pass out of the dual detector according to the invention.

After assembly of the additional components of the viscosity detector within the aluminum block 70, the channels in the block were recast in solder and the device reassembled.

The line from the low pressure end of the capillary to the bottom of the differential refractive index (DRI) detector stage was about 15 cm. of 0.01 inch ID tubing (7.6 ul). This arrangement affords good temperature stability (most of the mass of the dual detector is used as thermal ballast, stabilizing both), and at the same time, minimizes both the volumetric offset between the detectors and the sample back-mixing during transport between detectors.

As another factor involved in the present invention, it is important to keep the volume of the two detectors as identical as possible so that no corrections need be considered during the workup of the collected data. Typically, the volume of the offset is about 7.6 ul; the volume of the DRI detector is about 10 ul, with the tubing volume being about 3.6 ul.

As will be understood by those of ordinary skill in the art, the above configuration represents merely one example of the present invention. The essential characteristics of the dual detector include the incorporation of the DRI and differential pressure transducers in the same instrument, housed in a common thermal sink in "close-coupled" proximity. By the term "close-coupled" proximity is meant to include a volumetric offset in the range of about 0-100 ul. The above-described dual detector configuration achieves the following features. Temperature variation during viscosity and mass measurement is avoided. Incorrect accommodation of the volumetric offset between the two detectors is avoided. Sample dilution during transport between the two detectors is eliminated.

J. THE ELUTION VOLUME DETECTOR

As mentioned above, determination of elution volume represents the most critical measurement in any chromatographic determination of molecular weight distribution of a polymeric system. For modern columns which possess active volumes in the range of 2–5 ml, elution volume should be reproducible to within 10–25 ul. The present inventors have tested a system suitable for providing elution volume measurements to that degree of accuracy. The results are described in an article published in *Analytical Chemistry*, 55: 428–432 (1983), incorporated by reference herein. This device, a thermal pulse precision flow meter, operates by the simple timing of the passage of a thermal pulse through a well-defined volume, thereby generating microprocessor compatible output. Typical thermal pulse flow meters are described in U.S. Pat. No. 4,335,616 to Oliva et al.; U.S. Pat. No. 4,458,709 to Springer; and described by Miller, T. E. et al., *Anal. Chem.*, 54: 907–910 (1982) and in U.S. Pat. No. 4,491,024, all incorporated by reference herein.

In order to use a thermal pulse flow meter, it is necessary to determine values for the two constants which, along with flow rate, control the elapsed time between injection of thermal pulses in one part of the system and its detection downstream. This is accomplished by collected a number of these elapsed times while concurrently carrying out accurate measurements of the flow rate. A convenient technique for generation of this type of data is to direct the effluent from the system into the bottom of an autozeroing burette of well-characterized volume. The elapsed time between each of approximately 200 pulses is collected and subjected to standard regression analysis, yielding a statistically defined thermal pulse time of flight. During the same period, the time to fill the burette from the 10.00 ml. mark to the autozeroing point is measured with an electical timer accurate to 0.1 second. By carrying out such experiments over a variety of pump settings, it is possible to collect values for observed flow rate and time of flight (T(eff)). The results may be analyzed according to the relationship reported by Miller, T. E. et al., supra:

$$T = V_{cell}/f + K$$

where
T = period between thermal pulses
f = flow rate
K = thermal pulse cell constant
$V_{cell}$ = thermal pulse cell volume Once the cell constants have been measured, the flow meter is used to measure flow rate by using the elapsed time T(eff) in a rearranged form of the above equations, said rearranged equation being:

$$f = V_{cell}/(T - K)$$

followed by conversion to volume through the relationship:

$$\Delta V = T*f = \frac{T}{T-K} * V_{cell}, \text{ and } V_i = \sum_{j=1}^{i} (\Delta V_j).$$

This manipulation is done immediately after collection of the analog and T(eff) data. The incremental calculated volume is added to all of the preceding volumes, resulting in a total measured elution volume.

The electronic arrangement for exciting and detecting the signal from the Validyne DP15 transducer, in the preferred embodiment, is a Validyne CD104 carrier demodulator. This device generates a 0–10 volt output for the pressure range covered by the various diaphragms available. For most of this work, a diaphragm with a 0–120 PSI operating range is suitable.

Figure 5:
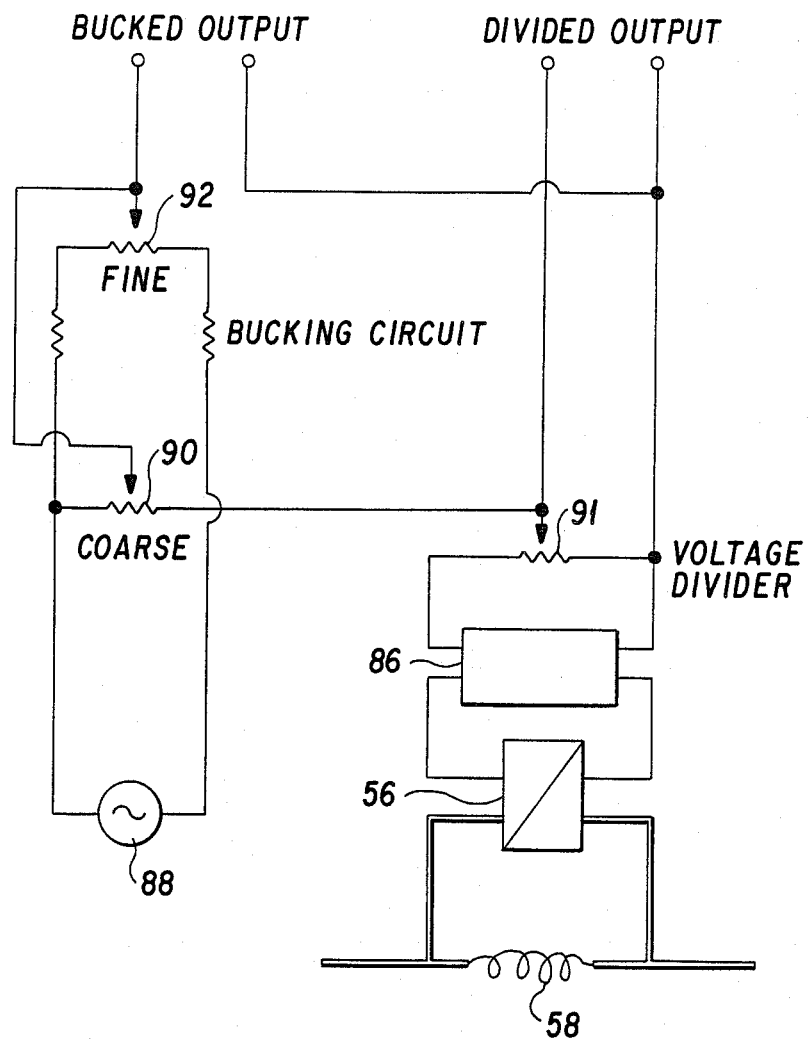
FIG. 5 is a schematic of the circuitry used to manipulate data from the differential pressure transducer used for viscosity determinations.

FIG. 5 is a schematic of the circuitry which is used to manipulate the output of the CD104 unit. The signal generated by the CD104 is first divided to some desired value (frequently 500 mv.) and the signal is then bucked to zero using a constant 10 volt source and associated circuitry (see FIG. 5). By bucking the divided voltage to essentially zero, it is possible to measure changes from the divided value using a chart recorder set at 10 mv. full scale. The ratio of the 10 mv. full scale reading and the value of the divided voltage provide a value for specific viscosity, or, after multiplication by 100, a value for the system noise. Dividing the output to 500 mv gives a full scale reading for a signal ratio (bucked/divided) of 0.02.

It will be appreciated by those skilled in the art that the relative variation in pressure drop across the capillary due to the presence of polymer samples in the solvent is small compared to the pressure drop due simply to viscosity of the solvent. This in itself would be no problem, except that it is desired to convert the analog pressure signals to digital values for subsequent analysis. As the dynamic range of available analog-to-digital converters is limited, if the entire value for pressure drop due to the solvent were to be converted to an analog value, little resolution would be left for the relatively minor variations in viscosity due to the presence of the samples therein. Accordingly, this would put an absolute limit on the accuracy of the system. Furthermore, of course, given the experimental apparatus shown, one would ordinarily have to measure the viscosity of the solvent in a calibration run, which is undesirable since one can never be certain that some of the process parameters which affect the viscosity, i.e., temperature, would not vary between the calibration and the experimental runs. Accordingly, it is desirable that measurement of the pressure drop due to the viscosity of the solvent itself be eliminated.

This can be accomplished according to the circuit of FIG. 5 as follows. The capillary 58 and the differential pressure transducer 56 are shown, as is the Validyne CD-104C carrier demodulator 86 which outputs a voltage signal in dependence on the difference in pressure across the two sides of the transducer 56. The output of the carrier demodulator 86 is reduced to a value within the dynamic range of the analog-to-digital converter used by a voltage divider, which simply comprises a potentiometer 91 (typically of 1,000 ohm value) connected across its terminals. The divided output is then supplied to a bucking circuit which comprises a voltage source 88, typically controlled to provide 10 volts. Two additional potentiometers 90 and 92 which may be of 1,000 ohm and 500 ohm values, respectively, provide coarse and fine adjustment of the bucking voltage. In this way, these two potentiometers allow the voltage-divided output of the system to be in the appropriate input range of the analog-to-digital device used.

Thus, the circuitry shown in FIG. 5 first voltage-divides the output of the demodulator 86 to a predetermined point, and then the bucking circuit adjusts the absolute value of this signal to be such that its zero value is relatively equivalent to the zero input value of the analog-to-digital converter used.

As will be subsequently discussed, an additional technique can be employed in completely removing the value of the contribution due to the viscosity of the solvent from the equation.

DATA ANALYSIS

As discussed above, the basic problem addressed by the present invention is that of determining the molecular weight distribution of a polymer sample. This may be accomplished as follows.

As is well understood, the intrinsic viscosity [n] of the polymer is equivalent to the specific viscosity of the solution divided by the concentration C of the polymer in the solution:

$$[n] = n_{sp}/C$$

The concentration C can be measured using any suitable mass detector; in the preferred embodiment, a differential refractometer is used. The specific viscosity $n_{sp}$ can be measured using a viscometer, allowing determination of the intrinsic viscosity [n].

The Benoit equation then relates the so-called hydrodynamic volume A of the particle (the size of the polymer particle in solution) to the intrinsic viscosity and the molecular weight as follows:

$$A = [n]MW$$

Having determined the intrinsic viscosity [n], one can then determine the molecular weight MW using values for the hydrodynamic volume developed by calibration of the SEC columns using polymers of known characteristics, all as described above. In practice, one simply monitors the elution volume and correlates this to the appearance of peaks in the signal output by the mass detector indicating the presence of polymer samples.

Having thus determined the hydrodynamic volume of the polymer, one can derive the molecular weight MW using the value previously derived for the intrinsic viscosity [n]. The result is a series of pairs of values for intrinsic viscosity and the corresponding molecular weight. These can then be subjected to regression analysis leading to values for K and a in the Mark-Houwink equation $[n] = K(MW)^a$, thus generating the Mark-Houwink coefficients K and a, in accordance with the objects of the invention discussed above.

As discussed briefly above, applicants have discovered that the specific viscosity $n_{sp}$ can be determined simply as a function of the pressure drop across the capillary, when the polymer in solution is passing through the capillary. This result is surprising because the specific viscosity $n_{sp}$ is generally expressed as follows:

$$n_{sp} = \frac{n(\text{polymer + solvent}) - n(\text{solvent})}{n(\text{solvent})}$$

Ordinarily, evaluation of this equation would involve measurement of the viscosity by equating it to the pressure drop across a capillary. One would expect that a value would have to be found for the denominator which would require measurement of the pressure drop due to the solvent alone. This could be carried out in a background or setup run, of course, but then one would never be sure that the pressure was exactly the same. Clearly, it would be desirable to avoid this step. Moreover, the applicants have found that the variation in pressure drop due to the presence of the polymer is extremely small, especially as compared to the overall pressure drop, because the amount of the polymer in the solvent is typically much less than 2%. In their experimental work, the applicants used conventional analog-to-digital converters for interfacing the experimental apparatus to computers for analyzing the data, plotting the results, and preparing the best fit analysis to determine the Mark-Houwink coefficients. Their analysis revealed that the numerator of the above equation is very small compared to the denominator and that if the entire dynamic range of the analog-to-digital converters available were to be devoted to digitizing the value for the denominator, the resolution provided for digitizing of the numerator would be very limited. The applicants therefore experimented with providing compensating voltages so as in effect to cancel out the pressure drop due to the solvent from the system, and found that measurement of the pressure drop due to the solvent could be totally eliminated. Therefore, the specific viscosity $n_{sp}$ is directly proportional to the numerator, thus requiring measurement of only the numerator. Hence, analog-to-digital conversion is required only of the pressure drop measured with respect to the polymer sample itself.

The detailed analysis of this discovery is as follows.

For laminar flow, the pressure drop $\Delta P$ across a capillary is given by:

$$\Delta P = \frac{8fln}{\pi r^4}$$

where
  n = viscosity of the solution;
  l = length of the capillary;
  r = radius of the capillary; and
  f = flow rate.

The specific viscosity $n_{sp}$ is expressed as follows:

$$n_{sp} = \frac{n(\text{polymer + solvent}) - n(\text{solvent})}{n(\text{solvent})}$$

If f, l, and r are constant, $\Delta P = kn$; therefore:

$$n_{sp} = \frac{\Delta P(\text{polymer + solvent}) - \Delta P(\text{solvent})}{\Delta P(\text{solvent})}$$

or $$n_{sp} = \frac{\Delta P''}{\Delta P}$$

where $\Delta P'' = \Delta P(\text{polymer+solvent}) - \Delta P(\text{solvent})$, and $\Delta P = \Delta P(\text{solvent})$.

For any volume increment $V_{inc}$:
P = The output of the VDP detector in the absence of polymer (i.e., prior to sample injection).

This output is arbitrarily divided to some convenient number, $P_0$. The output signal is then bucked to approximately 0.0 mvolts, so that a 0 to 10 mvolt analog-to-digital converter can be used to collect data reflecting the relatively small variations in the VDP detector output. The analog-to-digital converter used in the experimental apparatus has a 0.005 mvolt resolution so that 10.00 mvolts will correspond to 2000 counts.

$$P'' = h_{vdp} * \frac{10.00 \text{ mvolts}}{2000 \text{ counts}}$$

where $h_{vdp}$ = height of the VDP peak in A/D counts, i.e., the output of the viscometer.

Let $X = \frac{10.00}{P_0} * 100$, i.e., X is the percentage of the full scale output, $P_0$, represented by 10.00 mvolts Then $$P'' = h_{vdp} * \frac{X}{100} * \frac{1}{2000} * P_0$$

and $$n_{sp} = \frac{h_{vdp}}{P_0} * \frac{X/100}{2000} * P_0 = h_{vdp} * \frac{X/100}{2000}$$

$$= h_{vdp} * (VDP)_{constant}$$

X is a constant determined by the values of the resistors in the voltage divider circuitry; $(VDP)_{constant}$ is discussed below.

For example, if the VDP detector output were divided to $P_0 = 500$ mvolts, then X = 2% (10.00 mvolts = 2% of the full scale $P_0$ value) and $n_{sp} = h_{vdp} * 10^{-5}$.

Accordingly, the specific viscosity $n_{sp}$ can be determined simply by measurement of the pressure drop across the capillary due to the polymer sample in solvent.

Figure 11:
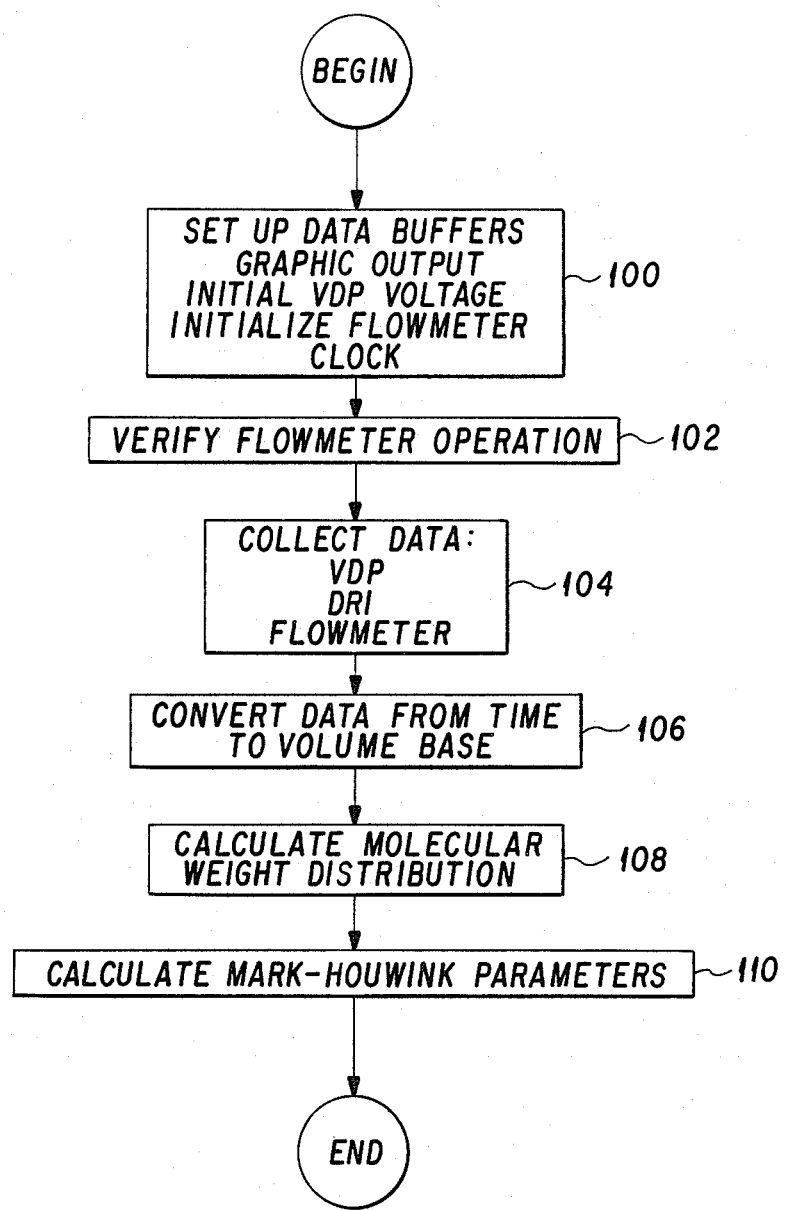
FIG. 11 is an overview block diagram of the analysis of the data according to the invention.

FIG. 11 is a block overview of the steps taken in processing of the data gathered in an experiment as described above to yield molecular weight data. At step 100, various parameters are initialized, data buffers are set up and the operator chooses the desired graphic format for the output from a variety of options. At step 102, operation of the thermal pulse flow meter described above is verified. As described below, data from this extremely accurate flow meter is used to convert data which is measured at regular intervals of time to data equivalent to regular intervals of volume, which is the correct variable to use for GPC/SEC subsequent processing steps.

The experiment then begins at step 104. In general, two channels of data along with a flow meter pulse channel are stored. The data channels include data taken at 40 ms. intervals from the viscosity detector (VDP) and the mass meter (in the preferred embodiment, a differential refractometer (DRI)). The technique of making such regular measurements is referred to in the appended claims as "progressive" measurement. The state of the flow meter is recorded at 40 ms. intervals. The first two inputs mentioned, from the VDP and DRI, are voltages respectively proportional to the pressure drop across the differential pressure transducer and the differential refractive index of the solution, a measure of its mass.

As described above, the thermal pulse flow meter comprises two thermisters, one of which is energized to impart a thermal pulse to a "slug" of the liquid flowing by the thermister at that time, and a second thermister which detects the passage of this slug, hence providing a very accurate indication of the time taken by that sample of liquid to flow between thermisters. The output of the flow meter is the bistable signal output by the second thermister, simply indicating whether a thermal pulse of elevated temperature was being detected at that moment or not. As mentioned, the signal from the second thermister is sampled every 40 ms., as are the VDP and DRI outputs.

The data is converted at step 106 to data values which are equivalent to samples taken at equal increments of volume as the sample fluid passes through the analysis system, using a process detailed below.

The next step at 108 is the calculation of the molecular weight distribution $MW_i$, followed by the calculation of the Mark-Houwink parameters at step 110, and calculations of the molecular weight moments, all as discussed below.

As will be understood by those skilled in the art, while it is most convenient to record data, that is, to store values for an analog signal, at regularly spaced intervals of time, it is more correct in processing operations to have data available at equal increments of volume. If the flow rate through the system is constant, of course, no conversion need be made. However, this is usually not the case.

Figure 12:
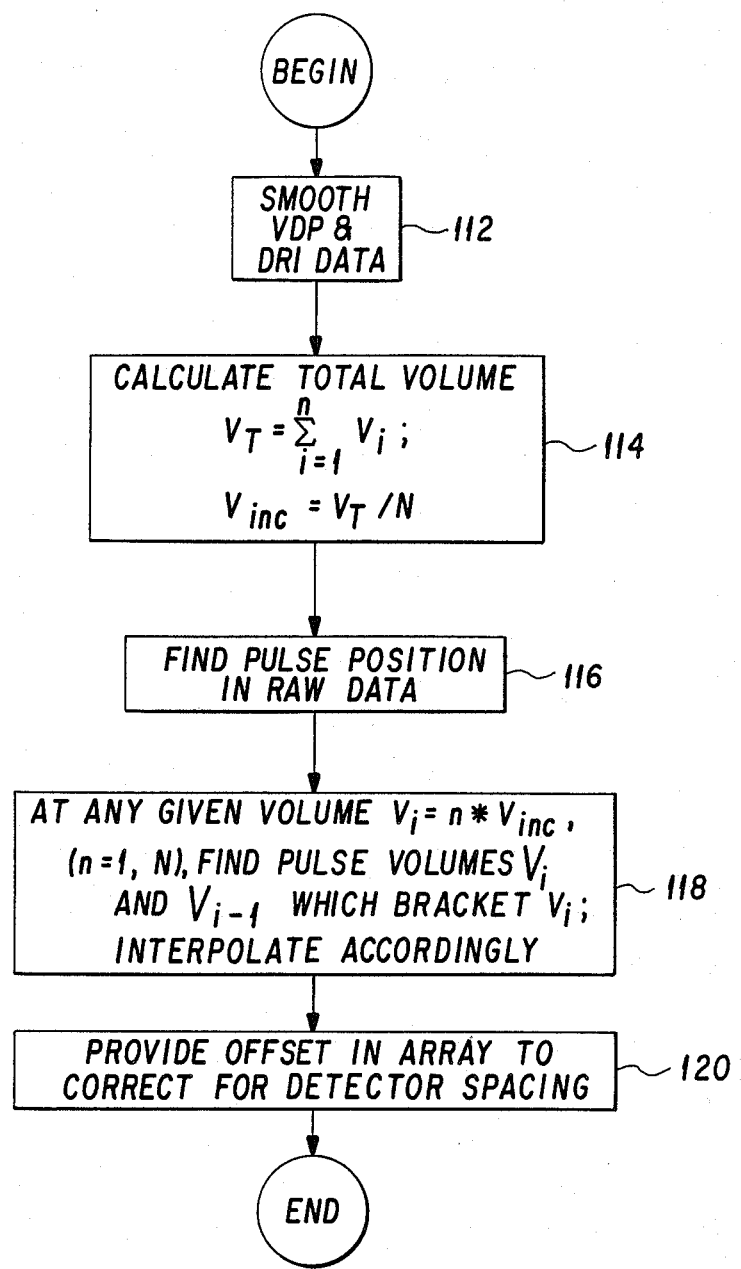
FIG. 12 is a block diagram showing details of the conversion of the data recorded during an experiment from a time base to a volume base.

FIG. 12 is a block diagram showing how the time based data originally recorded can be converted to volume based data. As adverted to above, this conversion is performed using data generated by the thermal pulse flow meter 24 described above, the bistable output of which is monitored at the same intervals as are the analog signals indicative of viscosity and of mass of a given sample, that is, the VDP and DRI output signals, respectively.

The conversion process begins at 112 with smoothing of the VDP and DRI data, which may be performed in conventional fashion. The present inventors have found a 25 point Savitzky-Golay digital filter to be useful in this process. At step 114, the total volume $V_t$ is calculated by summing over all the individual volumes measured by the flow meter during the experiment. An incremental volume $V_{inc}$ is then calculated by dividing the total volume $V_t$ by the number N of volume samples to be processed.

At step 116, the output of the flow meter is examined to determine the position of the pulses in the smoothed data: the bistable output of the flow meter is examined to determine when its output state changed, i.e., when thermal pulses were detected. The thermal pulses are generated, as mentioned above, by supplying a small amount of current to a first thermister. These impulses are provided at extremely regular intervals of elution volume, as determined by monitoring the time taken for fluid to flow through the flowmeter and adjusting the timing of the thermal pulses accordingly. Accordingly, the output signal at the time of detection of the thermal pulses can be used in the conversion of the data from time base to volume base. Typically, the detection of a pulse will fall between a pair of measurements for both VDP and DRI values.

The specific viscosity corresponding to each element in the refractive index array is calculated by deriving the offset corrected value from the VDP signal and using this offset to obtain the linearly interpolated VDP value. This value is then divided by the corresponding DRI value to obtain the appropriate specific viscosity value.

For example assume that the volume offset is 35 ul and the total elution volume is 12.0 ml. For an 8K data array, the volume increment $V_{inc}$ will be set to $12*10^3/8191 = 1.465$ ul. Thus, the volume offset $V_{off} = 23.89 * V_{inc}$.

Thus, for example, at element 100:

$$n_{sp} = \frac{h_{vdp100} - 23.89}{h_{dri100}} * \text{viscosity constant}$$

$$h_{vdp76.11} = h_{vdp76} + 0.11(h_{vdp77} - h_{vdp76})$$

The interpolated values for the VDP and the DRI data are then written to volume corrected files for use in subsequent processing operations.

Finally, at step 120, volume offset between the DRI and the VDP detectors is compensated for simply by adjustment of one of the series of data samples with respect to the other in the arrays in which they are stored so that the values stored in corresponding positions of each of the arrays correspond to the same sample of fluid. As discussed above, however, in the preferred embodiment of the invention, the actual volume between the two detectors is very small such that the correction needed to be made at this stage is relatively minor. Typically, using an array of 8,192 sample values, the shift is only on the order of 20–30 array positions.

Figure 13:
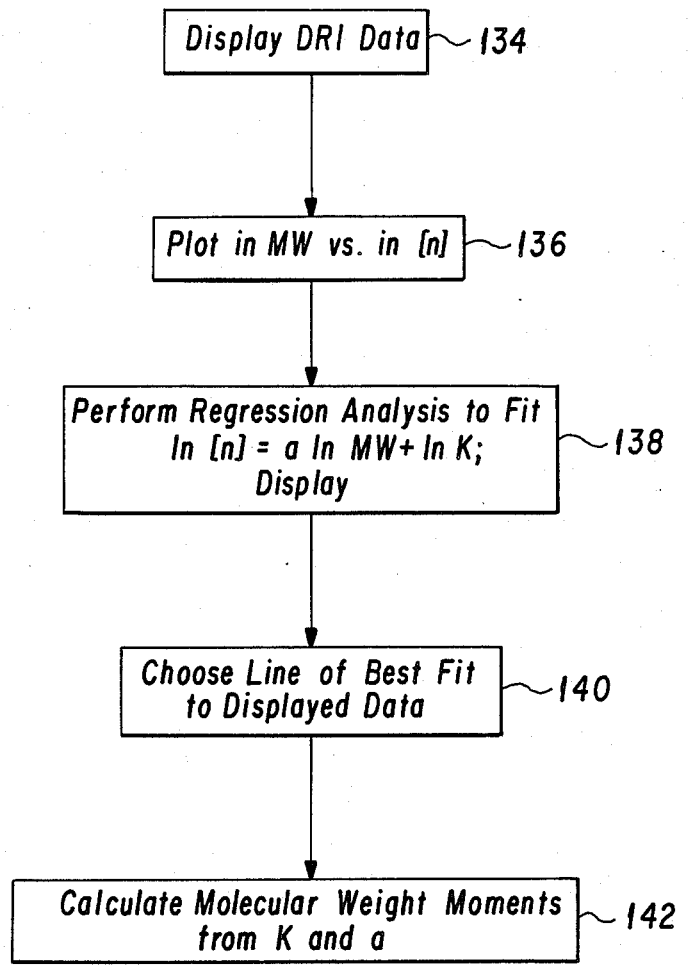
FIG. 13 is a block diagram showing details of the calculation of the molecular weight data according to the method of the invention.
Figure 14:
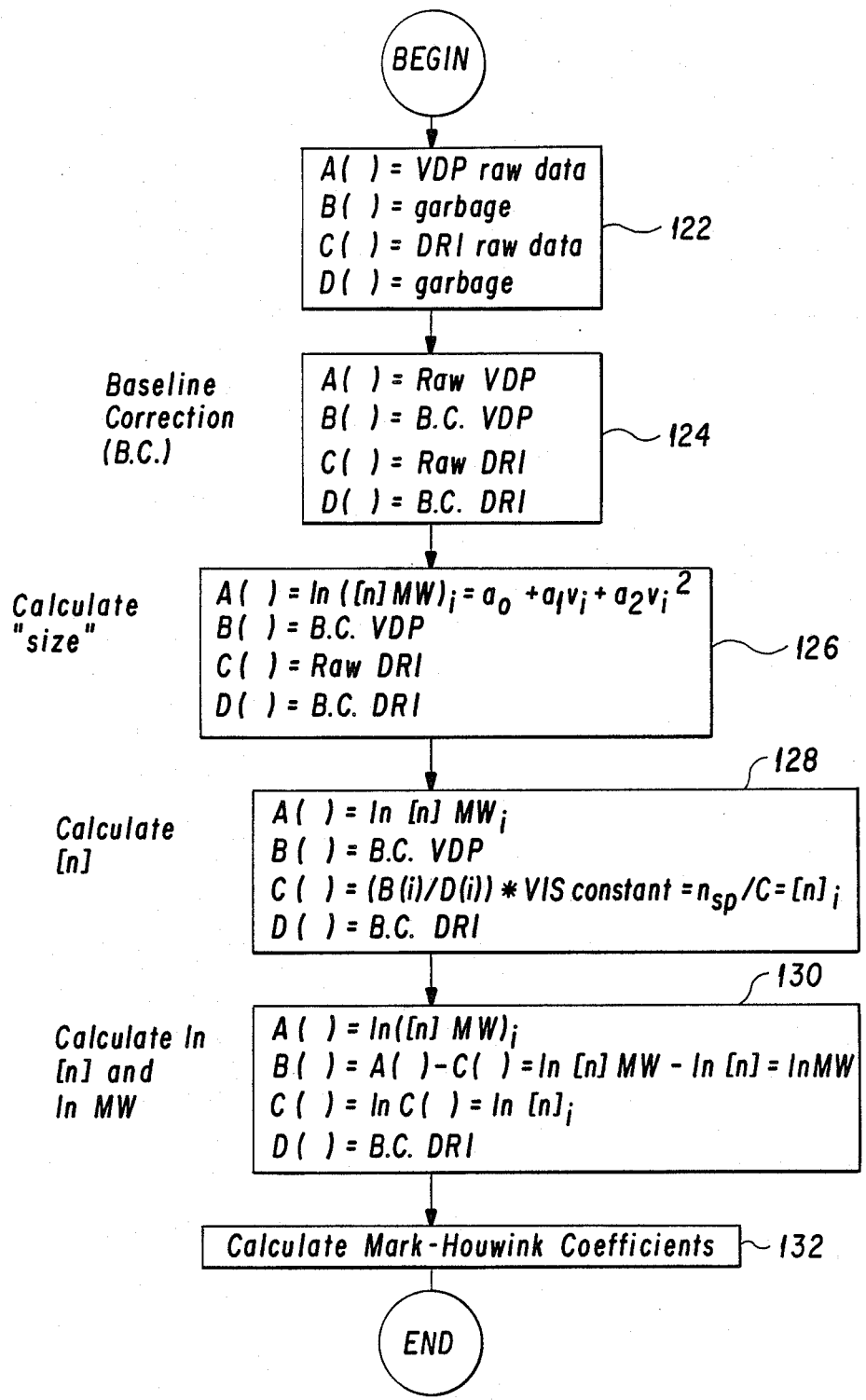
FIG. 14 is a block diagram showing the derivation of Mark-Houwink and other conventional coefficients from the viscosity and molecular weight data.

FIG. 13 is a block diagram describing the calculation of the molecular weight data from the VDP and DRI raw data, which has been converted to volume data and corrected for the volumetric offset of the two detectors, as described above. The process involves generally the use of four data arrays indicated in FIG. 13 as A( ) to D( ). These arrays are all of equal length and are used for storing the values of variables used in the processing operation. FIG. 14 shows the contents of the four arrays A( ) to D( ) at five stages. A legend outside of each box indicates the step which is performed at that stage, while the indication in the box shows what is contained in each of the four arrays at the conclusion of the step. Thus, at the beginning of the processing at step 122, array A(_)contains the VDP raw data, array B(_)contains "garbage"—that is, no meaningful data—, array C(_) contains the raw DRI data, and array D(_) also contains "garbage".

At step 124, baseline correction is performed. By this is meant that the contribution to the VDP and DRI data of the solvent is eliminated. This is done by plotting the raw VDP and DRI data successively on the operator's screen. Typically, the data is a bell shaped curve with asymptotic tails at either end. The operator is provided with a movable line on his screen and aligns it with the flat tails of the data, delimiting the baseline. Hence, the line corresponds to the value of VDP and DRI contributed by the solvent. A value corresponding to the data value at the baseline is then simply subtracted from the values stored in the A( ) and C( ) arrays, to yield the baseline-corrected values stored at B( ) and D( ), respectively. The voltage dividing circuitry, as discussed above, causes the voltage signal VDP due to the pressure drop across the capillary to be a full-scale signal with respect to the dynamic range of the analog-to-digital converters used, and the bucking circuit causes it to be properly located with respect to the input signal range acceptable by the analog-to-digital converters used. Baseline correction then is used to remove any additional contribution to the viscosity signal due to the solvent not removed by the bucking circuitry.

At step 126, the natural logarithm of the intrinsic viscosity times the molecular weight for each volume sample $V_i$ is calculated using, for example, the following relation:

$$\ln ([n]MW)_i = a_0 + a_1 v_i + a_2 v_i^2$$

The coefficients $a_0$, $a_1$ and $a_2$ are calculated using data gathered in the calibration operation described above in which a sample of a well characterized polymer, such as a conventional polystyrene sample, is used to calibrate the various elements of the system. $V_i$ is simply N (the element number in the array) times the incremental volume $V_{inc}$.

At step 128, the intrinsic viscosity [n] of each sample is calculated by dividing the base line corrected, offset adjusted, VDP data value stored in array B(_) by the base line corrected DRI data value stored in array D( ), multiplied in each case by a constant (referred to on the drawing as the VIS constant). This is equivalent to dividing the specific viscosity by the concentration, hence yielding the intrinsic viscosity according to the relation $[n] = n_{sp}/C$. The result is stored in array C( ).

The value of the VIS constant is determined by division of the VDP constant by the DRI constant. These latter two constants are derived as follows. The DRI constant is equal to the sample concentration in weight percent times the sample size and the solvent density, all of which are known, divided by the total DRI peak area (the sum of all the sample values taken in the DRI measurement) times 1,000. The VDP constant is calculated as follows. X, the value referred to above, determined by the resistances of the voltage divider used to compensate the VDP signal for the pressure drop across the capillary due to the presence of the solvent, divided by 100, is divided by the number of counts which represent 10 mv, thus accounting for the resolution of the analog-to-digital converter. In the example given, the maximum count is 2047 which equals 10.235 volts, and X represents the ratio of 10.00 mvolts to $P_0$.

The processing described in connection with step 128 thus calculates an actual value for the intrinsic viscosity [n] of each of the samples.

At step 130, the natural logarithms of the intrinsic viscosity and of the molecular weight are calculated. First, each element in array C( ), which is the intrinsic viscosity $[n]_i$ of the ith sample, is replaced by the natural logarithm thereof. This value is then subtracted from the corresponding element in array A( ), the natural logarithm of the intrinsic viscosity times the molecular weight, resulting in a value for the natural logarithm of the molecular weight, which is stored in array B( ). Simple exponentiation then provides an actual value for the molecular weight of the polymer in each sample, achieving this object of the invention.

At step 132, the Mark-Houwink coefficients may be calculated as discussed below in connection with FIG. 14.

FIG. 14 is a block diagram, as mentioned above, showing the derivation of the Mark-Houwink coefficients K and a. The Mark-Houwink equation, as discussed above, relates the intrinsic viscosity [n] to the molecular weight, as follows:

$$[n] = K(MW)^a$$

For any sample of a polymer of a given composition having variable molecular weight, the coefficients K and a will be constant. Accordingly, if a number of different values for the intrinsic viscosity and molecular weight are known, for example, calculated as described in connection with FIG. 13, values for the coefficients K and a can readily be calculated by curve fitting techniques. According to the preferred embodiment of the invention, this is done by displaying DRI data at step 134, plotting the natural logarithm of molecular weight versus that of the intrinsic viscosity at 136, and performing regression analysis to yield K and a according to the following relation:

$$\ln [n] = a \cdot \ln MW + \ln K$$

and then displaying the results at step 138. The operator chooses the line of best fit at step 140. At step 142 is indicated the fact that one can calculate additional parameters from K and a as desired, e.g. typical molecular weight moment data and the like, which are frequently calculated in the art using the Mark-Houwink coefficients.

Given the above detailed description of the method of practice of the invention, a skilled programmer would have no difficulty in programming any desired model of digital computer, using suitable analog-to-digital converters and the like, to perform the processing steps according to the invention.

Having now generally described the invention, the same will be more fully understood by reference to the following examples, none of which are intended to be limiting unless otherwise specified.

EXAMPLES

Referring again to FIG. 1, in the evaluation of the system which follows, the actual system elements employed were as follows:

1. pump 12 was an LDC Constametric III pump;
2. the damping system consists of an LDC Mark III damper, a Bourdon gauge, a Lichrom-A-Damp II damper, two Du Pont size-exclusion columns, and two Waters sensitivity filters, model no. 25480.

This configuration resulted in pump noise of 0.02% or a 99.4% reduction from the original undamped configuration.

The temperature coefficient of viscosity for many organic solvents is on the order of 1-2%/° C., and since it was anticipated that the system noise would be on the order of 0.02%, as much as possible of the system was thermostated. This was accomplished by using a 35 liter water bath in which the temperature was controlled by a YSI Model 72 Proportional Controller, Yellow Springs Instrument Co., Yellow Springs, Ohio. The bath, dual detector and all of the column and damping arrangements were held to within 0.005° C. using such an arrangement. It was necessary to use controlled temperature cooling water in order to achieve the desired temperature stability of the system.

EXAMPLE 1

Testing The Viscosity (VDP) Detector

As may be seen from the Pousieulle equation:

$\Delta P = fQ\eta$, for solvent only, changes in flow rate should produce changes in pressure drop in a linear fashion. The response of the viscosity detector under several different pump settings (flow rate settings) was examined.

Figure 6:
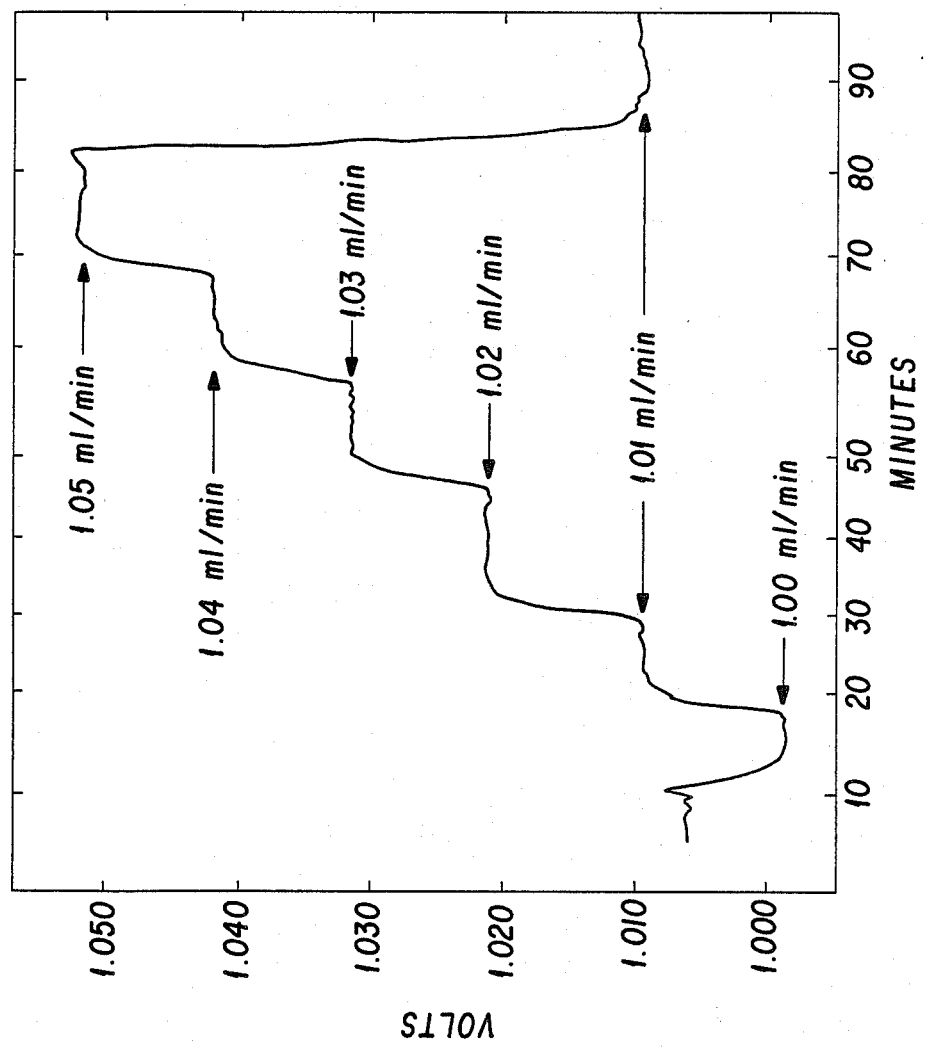
FIG. 6 is graphic representation of the response of the viscometer of the present invention to flow changes of a constant viscosity solution.

The results of this testing are depicted in FIG. 6. As may be seen from FIG. 6, the depicted behavior was completely consistent with the postulates to this point, and it was concluded that, for constant flow rate, any changes in output from the detector system were manifestations of changes in solution viscosity in the detector.

EXAMPLE 2

Determination of the "Effective" Volumetric Offset between the VDP and DRI Detectors The "effective" volumetric offset between the VDP and DRI detectors was determined by injecting a series of either narrow molecular weight distribution polymers or small molecules. After measuring the volumetric position of the peak maximum in the two detectors, it was concluded that the "effective" volumetric offset was approximately 35 ul. This value was expected to be different from the geometric offset (10–20 ul) because of the laminar nature of flow in the system. Laminar flow in small channels leads to parabolic concentration profiles.

In the following examples, samples were prepared as weight percent solutions in the appropriate solvents. Injections were carried out using Hamilton syringes and in all cases, no more than 30% of the sample loop was used for any injection.

EXAMPLE 3

Calibration of the System

Narrow distribution samples of polystyrene were obtained from Analabs, a unit of Foxboro Analytical, North Haven, Conn., Cat. No. CLA-155. Molecular weights for these samples were supplied with the samples and are listed in Table I below.

TABLE I

| | Narrow Polystyrene Samples | | |
|---|---|---|---|
| Sample No. | MW (light scattering) | MN Osmometry | MV Viscosity |
| 12C | — | 2,400 | 2,220 |
| 61110 | — | 3,570 | 3,600 |
| 80314 | — | 9,050 | 9,100 |
| 41220 | 20,400 | 15,100 | 17,440 |
| 60917 | 53,700 | 51,150 | 47,400 |
| 70111 | 93,050 | 92,600 | 98,700 |
| 50124 | 254,000 | 217,600 | 233,000 |
| 3B | 392,000 | 350,000 | 383,000 |
| 60914 | 598,800 | 600,250 | 607,200 |
| 61124 | 1,790,000 | — | 1,750,000 |

A highly characterized broad distribution polystyrene sample was obtained. This sample (polystyrene 1683) has been characterized by GPC, Ultracentrifugation, light scattering and by coupled GPC low angle laser light scattering (LALLS). Additionally, the incremental molecular weight-percent composition profile has been determined as carefully as possible. The sample is identical to the one used in ASTM method D3536-76 and has been submitted to the National Bureau of Standards for certification as a NBS polymer standard.

The variously measured molecular weight distribution parameters of polystyrene 1683 are listed in Table II:

TABLE II

| | Polystyrene 1683 | | |
|---|---|---|---|
| Technique | MW | MN | MZ |
| GPC(a.) | 250,000 ± 4,000 | 100,000 ± 3,000 | 431,600 |
| Ultracentrifuge | 250,000 | 100,000 | — |
| Light Scattering | 256,000 | — | — |
| LALLS | 252,000 | — | — |

(a.) Narrow standard calibration. Results from 30 analyses.

Branched Polystyrenes.

Experimental samples were obtained. These samples were prepared by polymerization in the presence of controlled amounts of divinyl benzene (DVB). The resulting polymers have been characterized by conventional (polystyrene equivalent) GPC, SEC- LALLS, and whole sample LALLS. The results are shown in Table III.

TABLE III

| | | Branched Polystyrene Samples | | |
|---|---|---|---|---|
| Sample | ppm DVB | MV (conv.) | (MW(SEC-LALLS) | MW(LALLS) |
| GP0 | 0 | — | — | — |
| GP78 | 78 | 287,000 | 351,100 | 331,000 |
| GP175 | 175 | 271,000 | 315,000 | 314,000 |
| GP325 | 325 | 254,000 | 317,000 | 313,000 |

Secondary Standards.

Several other "characterized" polymers were obtained from commercial sources. The supplier and quoted molecular weight parameters are listed in Table IV.

TABLE IV

| | Secondary Standard Polymers | | | |
|---|---|---|---|---|
| Polymer | Sample # | Supplier | MW | MN |
| Polycarbonate | 035C | SP2(a) | 33,800 | 13,400 |
| Poly-2-6-dimethyl-4-phenylene oxide | 126C | SP2 | 244,000 | 32,000 |
| Polydimethylsiloxane | 145C | SP2 | 103,400 | 43,900 |
| Polymethylmethacrylate | 037C | SP2 | 60,600 | 33,200 |
| Polystyrene | 039C | SP2 | 321,000 | 84,600 |
| Polyvinylacetate | 024C | SP2 | 195,000 | 47,700 |
| Polyvinylacetate | 15733 | PSI(b) | 435,000 | — |
| Polyvinylbutyral | 15734 | PSI | 116,000 | — |
| Polyvinylchloride | 038C | SP2 | 83,500 | 37,400 |
| Polyvinylchloride | 15735 | PSI | 83,500 | — |
| Polyvinylfluoride | 15736 | PSI | 126,000 | — |
| Polyvinylformal | 15737 | PSI | 47,200 | — |

(a) Scientific Polymer Products, Inc., Webster, New York.
(b) Polysciences, Inc., Warrington, Pennsylvania.

Solvents.

All solvents used in this study were obtained from Burdick and Jackson and were of distilled in glass purity. Both the THF and CHCl$_3$ solvents contained small amounts of stabilizers.

RESULTS AND DISCUSSION

Calibration

System calibration in all instances reported here was accomplished using a broad standard technique (See Yau et al., supra, p. 294) and polystyrene 1683. In general, four to six injections of varying amounts of polymer were made and the collected data subjected to analysis using a model containing third order terms in both amount of polymer and elution volume. This resulted in several sets of calibration coefficients and equations. The most commonly used equations (i.e., most column configuration were adequately described by these forms) are shown below:

$$\ln(MW(1)) = f(V, V^2, V^3)$$

$$\ln(MW(2)) = f(V, V^2, V^3) \times f(ugm, ugm^2, ugm^3)$$

$$\ln(MW(3)[n]) = f(V, V^2, V^3) \times f(ugm, ugm^2, ugm^3)$$

Figure 7:
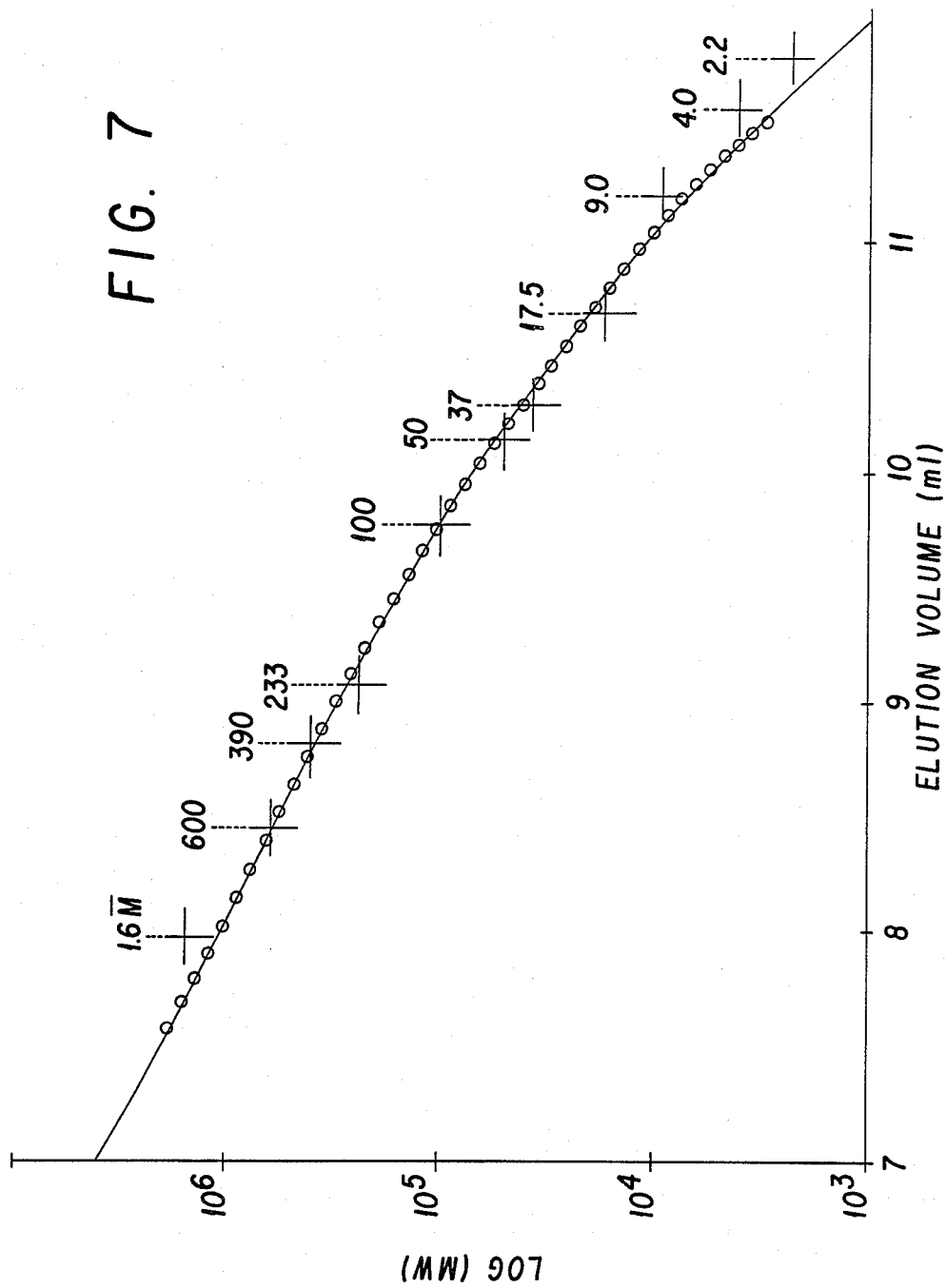
FIG. 7 is a graphic representation of the plot of the log molecular weight against elution volume of a broad standard, polystyrene 1683, developed in the calibration of the invention system.

For a column configuration consisting of a Waters E-high (Part No. 84397) followed by a Du Pont Bimodal-S pair (PSM-600 plus PSM-1000), this calibration approach led to the results shown in FIG. 7. In this Figure, the circles represent the forty-three characterized portions of polystyrene 1683, the solid line is the derived calibration line using coefficients from four different injections of polystyrene 1683 and represents the expected response for an injection of 180.2 ugm of polymer. The intersections of the crosses represent the observed elution volumes of 180.2 ugm of injected narrow standard samples for this same column arrangement. The agreement between narrow and broad polystyrene samples was completely satisfactory. This particular representation of the molecular weight is referred to as "conventional" since it is the more common technique used in laboratories not equipped to use the universal method of molecular weight measurement.

Figure 8:
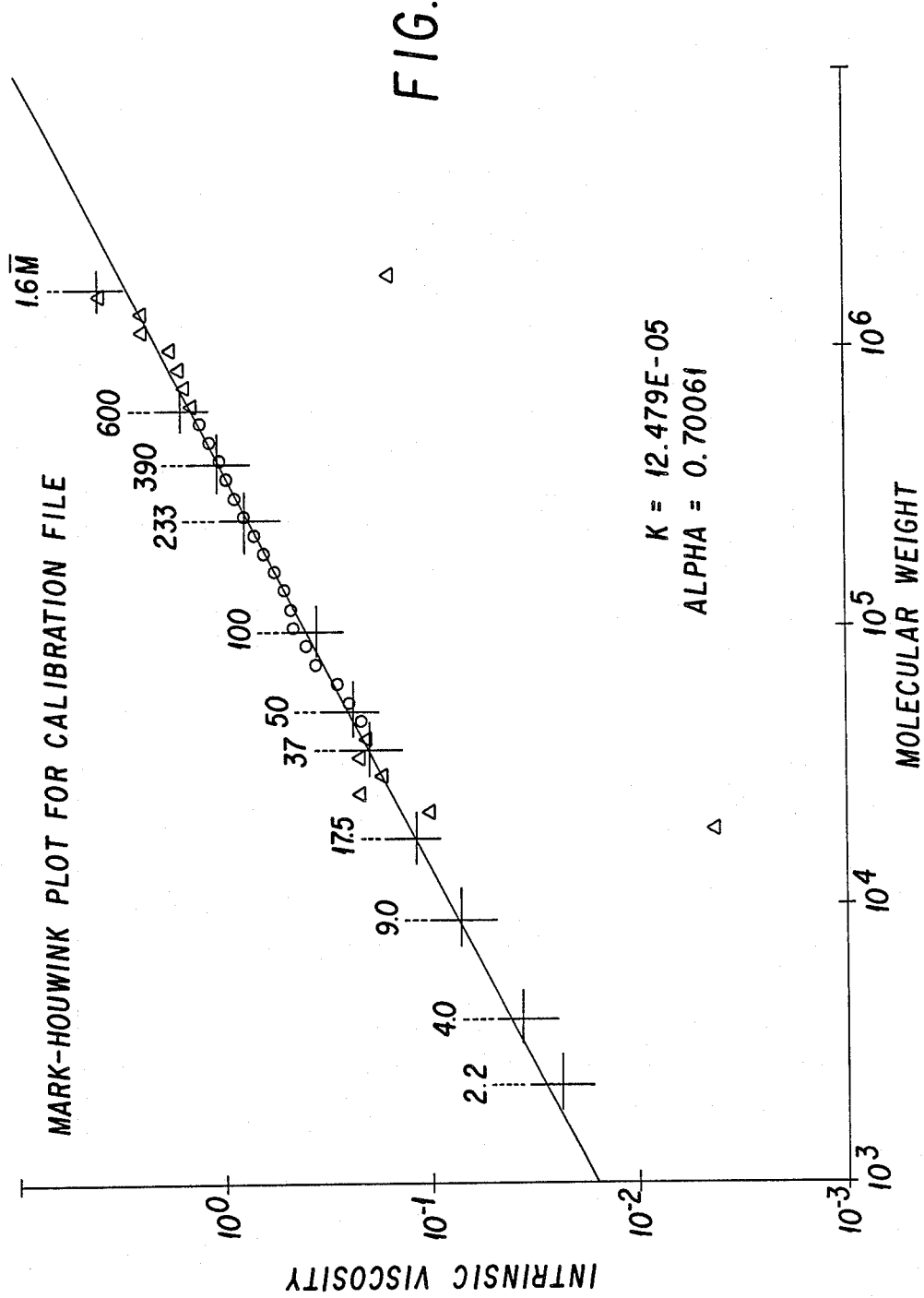
FIG. 8 is a graphic representation of a plot comparing Mark-Houwink values for narrow standard and broad standard polystyrene samples. The circles represent the broad standard parameters; the crossed lines represent the narrow standard parameters.

Since the technique automatically yields the intrinsic viscosity for narrow dispersity polymers, it is also possible to compare results for broad and narrow polystyrenes in terms of the Mark-Houwink relationship. This is shown in FIG. 8, in which the observed intrinsic viscosities for narrow standard polystyrene samples (crossed figures) are plotted along with the observed intrinsic viscosities for those portions of the polystyrene 1683 sample which provided recognizable signals in both the DRI and VDP channels (circles). The line in FIG. 8 is the regression line derived from the middle 90% of the data set from the polystyrene 1683 sample. The Mark-Houwink parameters for polystyrene were derived from this same portion of the data. Again, the correspondence of results from both broad and narrow polystyrene samples was excellent.

Figure 9:
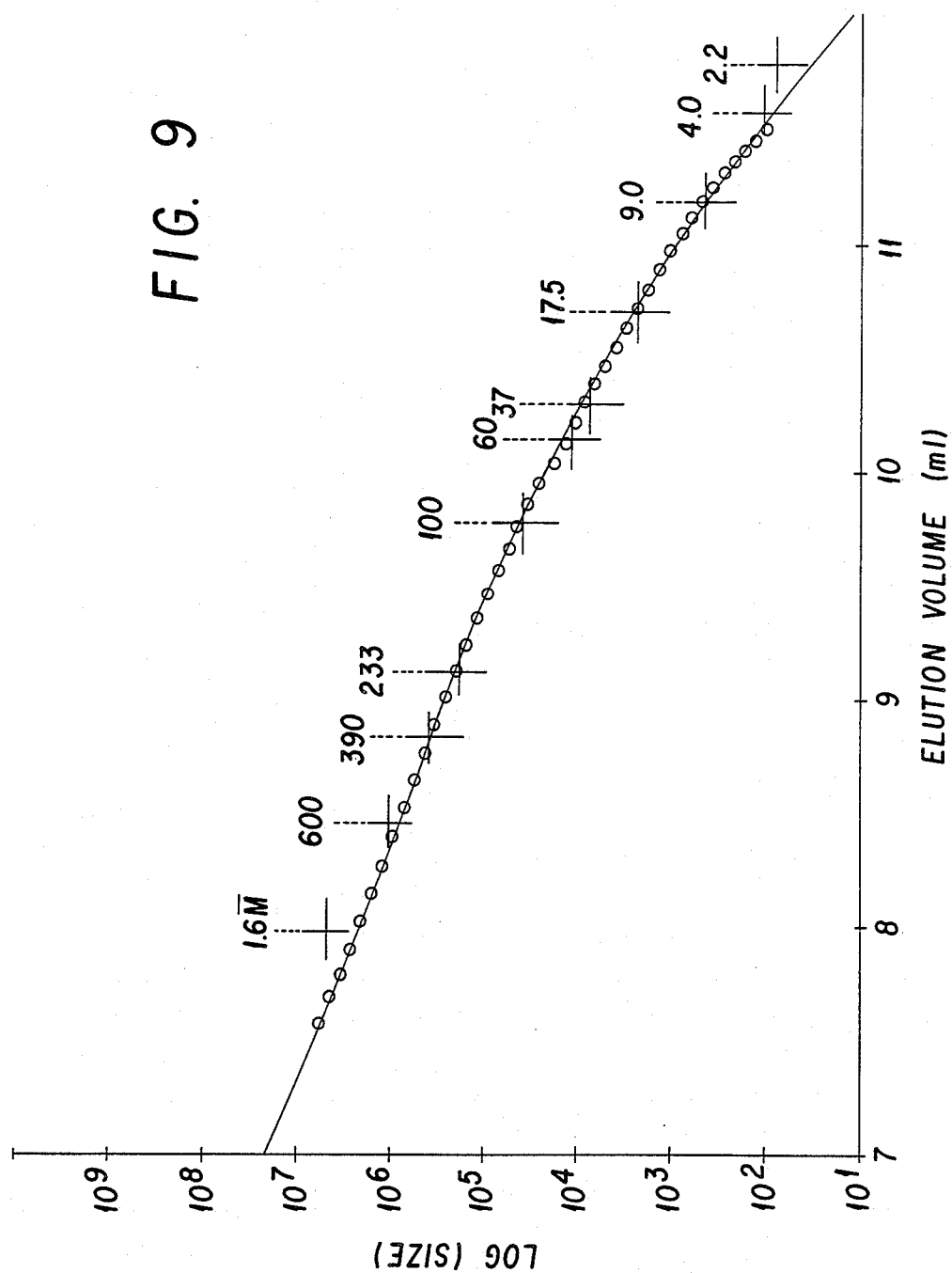
FIG. 9 is a graphic representation of the plot of the log of hydrodynamic volume against elution volume. The ordinate values were obtained from known molecular weight data and observed intrinsic viscosity data.

FIG. 9 is similar to FIG. 7 with the important distinction that the ordinate is derived from the known molecular weight and the observed intrinsic viscosity. Since it has already been shown that the agreement for both molecular weight and intrinsic viscosity is good for the two types of polystyrene, it was no surprise that the universal or Benoit plot was also satisfactory.

The results of Example 3 demonstrate that various column configurations can be adequately calibrated and that as long as the polymer loading on the columns is accounted for, that good correspondence between narrow and/or broad polymer samples can be achieved.

EXAMPLE 4

Analysis of Polystyrene 1683

By using the calibration coefficients and equations described above, it was possible to consider polystyrene 1683 as an unknown and to generate results for the various parameters available via this technique. Using a Du Pont Bimodal-S pair with THF as solvent (0.70 ml/min.), and several injections of polystyrene 1683 led to the results shown in Table V below.

TABLE V

| | Analysis of Polystyrene 1683 (C-6057-9, MW/1000) | | | | | | |
|---|---|---|---|---|---|---|---|
| Run No. | MW | MN | MZ | MV | [n] | $K \times 10^5$ | a |
| 1 | 256.2 | 95.4 | 452.8 | 222.0 | 0.679 | 39.0 | 0.606 |
| 2 | 248.8 | 99.7 | 433.8 | 218.9 | 0.690 | 30.6 | 0.628 |
| 3 | 248.3 | 102.0 | 425.8 | 220.5 | 0.696 | 24.8 | 0.645 |
| 4 | 250.7 | 102.8 | 428.2 | 226.0 | 0.670 | 13.9 | 0.688 |
| "truth" | 250.0 | 100.0 | 431.6 | 209.4 | 0.663 | 15.3 | 0.681 |
| a.m.* | 251.0 | 100.0 | 435.2 | 221.9 | 0.684 | 27.1 | 0.642 |
| s.d.** | 3.6 | 3.3 | 12.2 | 3.0 | 0.012 | 10.5 | 0.035 |
| r.s.d.*** | 1.4% | 3.3% | 2.8% | 1.4% | 1.7% | 38.9% | 5.4% |

*Arithmetic mean
**Standard deviation
***Relative standard deviation = $\frac{S.D.}{A.M.} \times 100$ In the Table, the "truth" was obtained from extensive data previously collected. It is readily apparent that all of the various parameters measured above are satisfactorily close to the "truth" for this particular polymer sample. The large standard deviation observed for the Mark-Houwink "k" value is probably due to the length of extrapolation involved in the analysis of that data.

For polystyrene at least, this technique resulted in completely satisfactory values for the various parameters derived from the data.

EXAMPLE 5

LALLS Analysis of Secondary Standard Polymers

Several commercially available "standard" polymer samples were obtained (see Table IV) and analyzed using a low angle laser light scattering device. A list of results as well as values obtained from the suppliers is shown in Table VI.

TABLE VI

| | LALLS Analysis of Commercial Polymers (MW/1000) | | |
|---|---|---|---|
| Polymer | MW(LALLS) | dN/dC (LALLS) (THF) | MW (supplier) |
| Polyvinylacetate | 216.0, 202.0 | 0.054 | 195.0, 435.0 |
| Polyvinylformal | 70.9 | 0.079 | 47.2 |
| Polyvinylchloride | 78.0 | 0.110 | 83.5 |
| Polyvinylbutyral | 55.8 | 0.084 | 116.0 |
| Polycarbonate | 20.5 | 0.185 | 33.8 |
| Polystyrene | 336.5 | 0.191 | 321.0 |
| Polymethylmethacrylate | 94.7 | 0.086 | 60.6 |

Rather surprisingly, of all these commercial "characterized" polymers, only polyvinylacetate, polyvinylchloride and polystyrene seem to be correctly labelled. Because of this discrepancy and because of confidence in the analyses, it was decided that the above LALLS results would be considered as correct in the following experiment.

EXAMPLE 6

Sec-[n] Analysis of Secondary Standard Polymers

Analysis of the series of secondary standard polymers shown in Table IV using a TSK-GMH6 column and THF at a flow rate (nominal) of 1.0 ml/min. was carried out using the broad standard calibration technique already described. The results of this study are shown in Table VII below.

TABLE VII

SEC-[n] Analysis of Secondary Standard Polymers
(C-0722-43, TSK-GMH6, THF, 1.0 ml/min., MW/1000)

| Polymer | ugm | dN/dC (a) | MW(3) | MW (LALLS) | MW (supplier) |
|---|---|---|---|---|---|
| Polycarbonate | 204.16 | 0.0955 | 29.3 | 20.5 | 33.8 |
| Polyvinylformal | 172.95 | 0.0375 | 77.5 | 70.9 | 47.2 |
| Polyvinylchloride | 188.47 | 0.0511 | 99.5 | 78.0 | 83.5 |
| Polystyrene | 181.22 | 0.0925 | 294.6 | 336.5 | 321.0 |
| Polymethylmethacrylate | 191.96 | 0.0437 | 109.5 | 94.7 | 60.6 |
| Polyvinylacetate-low | 205.57 | 0.0289 | 221.4 | 202.0 | 195.0 |
| Polyvinylacetate-high | 186.64 | 0.0253 | 208.9 | 216.0 | 435.0 |
| Polyvinylbutyral | 194.15 | 0.0408 | 70.8 | 55.8 | 116.0 |

(a) Calculated by dividing the observed DRI area by the ugm polymer injected.
(3) Derived using the "universal" approach of this invention.

Figure 10:
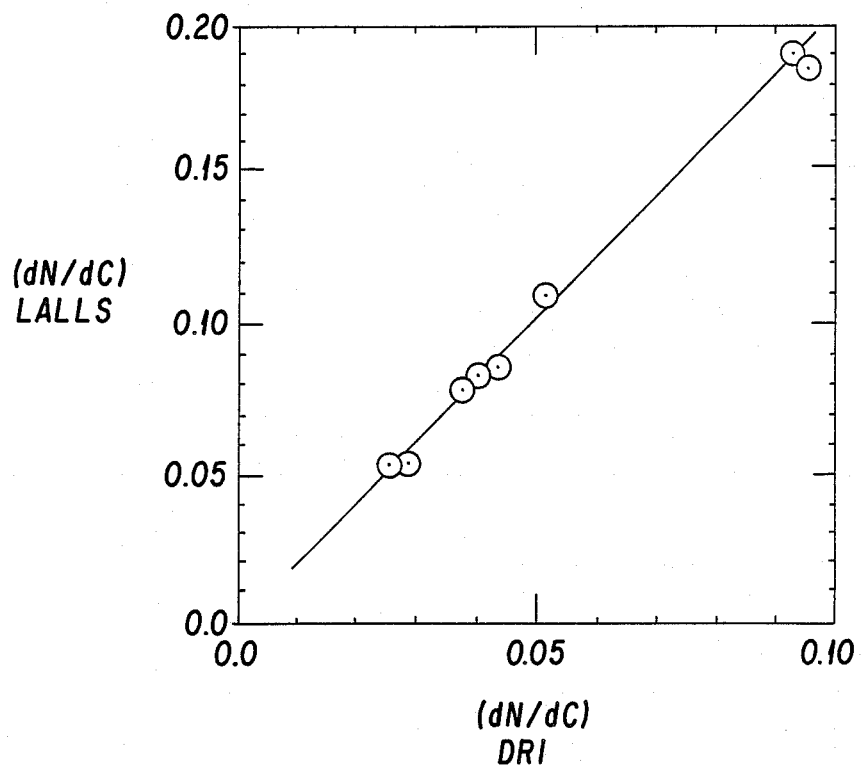
FIG. 10 is a graphic representation of a plot of dN/dC (obtained from a differential refractometer) against dN/dC (obtained from LALLS) for the family of polymers of Table VII.

It is of interest to note the values in the column labelled dN/dC. Since they are derived from the DRI output, it may be that they are related to the dN/dC values used during typical SEC-LALLS analysis of soluble polymers. To test this idea, a plot of (dN/dC) (DRI) against (dN/dC) (LALLS) for the family of polymers shown above was constructed. FIG. 10 shows this plot. The relationship depicted is nicely linear (r=0.997) with the least squares values for slope and intercept of 2.0654 and −0.0013, respectively.

Returning to the data shown in Table VII, it is apparent that this approach does yield reasonable values for all polymers examined. The variation from the "truth" is probably related to the small active volume used in these experiments (about 5.0 ml). Presumably, the use of more and/or better columns would result in more accurate results.

Using this column/solvent/flow rate combination results in values within 10-15% of the "truth" in a total elapsed time of about 15 minutes from injection to final results. This appears to be true for any soluble polymer.

EXAMPLE 7

Evaluation of a Mixed Resin Column

A similar experiment utilizing a column configuration consisting of two PL gel mixed resin columns and THF at a nominal flow rate of 1.0 ml/min., was next carried out. The results from examining the same family of polymers are shown in Table VIII below.

TABLE VIII

SEC-[n] Analysis of Secondary Standard Polymers
(C-0772-41, PLgel pair, THF, 1.0 ml/min., MW/1000)

| Polymer | ugm | MW(3) | MW(LALLS) | MW(supplier) | dN/dC |
|---|---|---|---|---|---|
| Polyvinylchloride | 188.47 | 89.4 | 78.0 | 83.5 | 0.0492 |
| Polymethylmethacrylate | 191.96 | 107.1 | 94.7 | 60.6 | 0.0380 |
| Polyvinylbutyral | 194.15 | 88.0 | 55.8 | 116.0 | 0.0293 |
| Polyvinylacetate-high | 186.64 | 200.4 | 216.0 | 435.0 | 0.0170 |
| Polyvinylacetate-low | 205.57 | 223.3 | 202.0 | 195.0 | 0.0312 |
| Polyvinylformal | 172.75 | 62.9 | 70.9 | 47.2 | 0.0312 |
| Polystyrene | 181.22 | 336.1 | 336.5 | 321.0 | 0.0851 |
| Polycarbonate | 204.16 | −19.2 | 20.5 | 33.8 | 0.0833 |

(3) Derived using the "universal" approach of this invention.

In this experiment, reasonable results were obtained. The average accuracy for the above sample was about 92%, which is well within an expected precision of ±5% for the LALLS and ±10% for the SEC-[n] results.

Again, the relationship between (dN/dC) (LALLS) and (dN/dC) (DRI) was nicely linear (r=0.998) with a slope of 1.9905 and intercept of 0.0168. These values were substantially similar to those observed using the TSK column.

EXAMPLE 8

Evaluation of Non-Polystyrene Gels

Next, attention was turned to the use of SEC columns which were not polystyrene gels. Aquapore-OH, which contains a glycerylpropyl-modified porous glass matrix, was evaluated as an example of a non-polystyrene gel.

The results from this particular system configuration are shown in Table IX.

TABLE IX

SEC-[n] Analysis of Secondary Polymer Standards
(C-0722-36, Aquapore-OH set(a.), THF, 1.0 ml/min., MW/1000)

| Polymer | MW(1) | MW(2) | MW(3) | MW(LALLS) | MW(supplier) |
|---|---|---|---|---|---|
| Polymethylmethacrylate | 92.3 | 84.3 | 123.3 | 94.7 | 60.6 |
| Polyvinylchloride | 148.1 | 136.1 | 94.8 | 78.5 | 83.5 |
| Polystyrene | 308.5 | 292.8 | 300.8 | 336.5 | 321.0 |
| Polyvinylacetate-low | 200.7 | 188.7 | 216.9 | 202.0 | 195.0 |
| Polycarbonate | 51.4 | 46.7 | 32.1 | 20.5 | 33.5 |
| Polyvinylbutyral | 118.3 | 108.6 | 69.8 | 55.8 | 116.0 |

TABLE IX-continued

SEC-[n] Analysis of Secondary Polymer Standards
(C-0722-36, Aquapore-OH set(a.), THF, 1.0 ml/min., MW/1000)

| Polymer | MW(1) | MW(2) | MW(3) | MW(LALLS) | MW(supplier) |
|---|---|---|---|---|---|
| Polyvinylacetate-high | 198.5 | 184.6 | 197.3 | 216.0 | 435.0 |
| Polyvinylformal | 92.4 | 83.7 | 66.9 | 70.9 | 47.2 |

(a.) Four column set consisted of 4,000, 1,000, 500 and 100 angstrom pore sizes.
(3) Derived using the "universal" approach of this invention.

In the above Table IX, MW values calculated via more conventional techniques are included as columns headed MW(1) and MW(2). MW(1) values were derived from a third order polynomial (in volume) to describe the ln(MW): elution volume profile. MW(2) values were derived from incorporation of the ugm dependence (third order polynomial) in a relationship similar to that of MW(1). MW(3) represents the values derived from the universal approach.

EXAMPLE 9

Evaluation of a Different Solvent, Chloroform

Since the underlying principle for all of this work indicates that the results should be independent of both column structure and solvent used, it seemd appropriate to examine the same family of polymers, the same column configuration and a different solvent. The solvent chosen was chloroform. The results of examining those polymers in the above family which are soluble in chloroform are shown in Table X.

TABLE X

SEC-[n] Analysis of Secondary Standard Polymers

| Polymer | MW(3) | MW(LALLS) | MW (supplier) |
|---|---|---|---|
| Polymethylmethacrylate | 112.3 | 94.7 | 60.6 |
| Polystyrene | 336.5 | 336.5 | 321.0 |
| Polyvinylbutyral | 59.0 | 55.8 | 116.0 |
| Polycarbonate | 39.4 | 20.5 | 33.8 |
| Polyvinylacetate-low | 205.1 | 202.2 | 195.0 |
| Polyvinylchloride (insoluble) | — | 78.0 | 83.5 |
| Polyvinylformal (insoluble) | — | 70.9 | 47.2 |
| Polyvinylacetate-high | — | 216.0 | 435.0 |
| Polydimethylsiloxane | 180.9 | — | 103.4 |
| Polyphenyleneoxide | 61.0 | — | 244.0 |

(3) Derived using the "universal" approach of this invention.

Examination of the results listed in these last two tables indicates that within ±8%, there is no apparent effect of solvent change on the derived molecular weight distribution.

EXAMPLE 10

Evaluation of Surface-Modified Porous Silica Columns

A series of experiments were also carried out using another set of columns which contained surface modified porous silica, Du Pont's Bimodal columns. Calibration and analysis were carried out at several different flow rates to determine what effect, if any, this might have on the obtained results. It was noted during these experiments that the DuPont columns were very susceptible to overloading, even at the low sample amounts (100–300 ugm) used for this work. The results from this study are contained in Table XI.

TABLE XI

SEC-[n] Analysis of Secondary Standard Polymers
(Du Pont Bimodal-S pair, THF, MW/1000)

| Polymer | MW(3) 0.7 ml/min. (a) | MW(3) 0.8 ml/min. (b) | MW(3) 0.9 ml/min. (c) | MW (LALLS) |
|---|---|---|---|---|
| Polymethylmethacrylate | 99.0 | 98.7 | 122.6 | 94.7 |
| Polyvinylbutyral | 66.2 | 58.8 | 75.4 | 55.8 |
| Polyvinylacetate-high | 223.2 | 230.6 | 221.5 | 216.0 |
| Polyvinylacetate-low | 203.6 | 223.4 | 234.1 | 202.0 |
| Polyvinylformal | 68.9 | 50.4 | 73.0 | 70.9 |
| Polystyrene | 304.4 | 251.7 | 326.3 | 336.5 |
| Polycarbonate | 33.7 | 47.2 | 32.3 | 20.5 |
| Polyvinylchloride | 84.4 | 84.3 | 81.9 | 78.0 |

(a) C-0657-11
(b) C-0625-43
(c) C-0657-26
(3) Derived using the "universal" approach of this invention There appears to be some problem at the high and low ends of this particular column set, which is probably derived from the distribution of pore sizes available. In general, however, the above results seem to be acceptable.

EXAMPLE 11

Branching Frequency Measurements

A series of long-branched polystyrene samples, prepared by incorporation of divinyl benzene (DVB) in the polymerization mixture, were also examined using this technique. The obtained molecular weight distributions and other derived parameters are shown in Table XII.

TABLE XII

Parameters Obtained For Long-Chain Branched Polystyrenes (MW/1000)

| DVB (ppm) | MW(a) | MW | MN | MZ | MV | [n] | kx 10⁵ | a |
|---|---|---|---|---|---|---|---|---|
| 0 | — | 288.9 | 122.9 | 479.4 | 256.9 | 0.7608 | 33.3 | 0.621 |
| 78 | 331.0 | 315.1 | 138.0 | 568.6 | 274.3 | 0.7335 | 38.3 | 0.604 |
| 175 | 314.0 | 295.7 | 108.3 | 613.3 | 247.3 | 0.6854 | 71.8 | 0.553 |
| 325 | 313.0 | 303.1 | 91.1 | 706.9 | 241.2 | 0.5971 | 61.6 | 0.555 |

(a) Obtained using LALLS. See Introduction section.

Using the method of Ambler, Mate and Purdon (*J. Polym. Sci., Poly. Chem.*, 12: 1759 (1974)), it is possible to estimate the number of branch points in the branched molecules listed above.

These workers used relationships derived by Zimm and Stockmayer (*J. Chem. Phys.*, 17: 1301 (1949)), who suggested that at high molecular weights, branching was proportional to molecular weight. These relationships manifest themselves in the intrinsic viscosities of the dissolved, branched polymers as follows:

$$[n]_{Branched}/[n]_{linear} = g^{\frac{1}{2}} \qquad \text{i.}$$

$$g = [(1+m/7)^{\frac{1}{2}} + 4m/9\pi]^{-\frac{1}{2}} \qquad \text{ii.}$$

where m is the number of branch points in any given molecule with intrinsic viscosity [n] branched. The branching frequency for a given molecular weight (λ) is defined as:

$$\lambda = m/M \qquad \text{iii.}$$

The ratio of branched and linear intrinsic viscosities can be arrived at several different ways. (1) the observed values can be used; (2) calculated values using the derived Mark-Houwink coefficients can be used; (3) smoothed values can be generated from plots of observed intrinsic viscosity versus ppm DVB in the system; and (4) smoothed values can also be generated from plots of Mark-Houwink derived values versus DVB in the polymer. The results from all of these approaches and the resulting branching frequencies for 300,000 mw polymer are shown in Table XIII below.

TABLE XIII

Branched Frequencies for DVB Branched Polystyrenes

| DVB (ppm) | [n](1) | [n](2) | [n](3) | [n](4) | (1) | (2) | (3) | (4) | (calc) |
|---|---|---|---|---|---|---|---|---|---|
| 0 | 0.761 | 0.839 | 0.768 | 0.832 | 0.00 | 0.00 | 0.00 | 0.00 | 0.00 |
| 78 | 0.734 | 0.775 | 0.728 | 0.795 | 0.25 | 0.60 | 0.38 | 0.31 | 0.36 |
| 175 | 0.685 | 0.768 | 0.679 | 0.749 | 0.83 | 0.68 | 1.03 | 0.84 | 0.81 |
| 325 | 0.597 | 0.673 | 0.602 | 0.679 | 2.74 | 2.34 | 2.76 | 2.08 | 1.50 |

(1) Using observed intrinsic viscosities.
(2) Using Mark-Houwink calculated 300,000 mw intrinsic viscosities.
(3) Using smoothed, observed values.
(4) Using smoothed, Mark-Houwink derived values.
(calc) Assuming a molecular weight of 300,000.

Comparison of the calculated and observed values for branch frequency in Table XIII seems to indicate that technique (4) yielded the most consistent results However, none of the other techniques led to values much different than those of technique (4), so the most straightforward technique, (1), is probably the method of choice.

In any event, the results do strongly indicate that long-chain branches can be measured and quantified using this approach.

This invention described here can be used to generate a wide range of valuable parameters which describe the molecular weight distribution of soluble polymeric systems.

The most common technique in use today only compares the molecular sizes of eluting components to those of a "standard" polymer of different structure. The results obtained from this technique are only relative and do not reflect the actual molecular weight of the polymer being examined. In addition, this technique is incapable of obtaining parameters which describe the configuration of the polymeric species in solution (the Mark-Houwink constants), or determining the presence or absence of long-chain branches in the system.

Another available technique for obtaining molecular weight distribution parameters utilizes a coupled low angle laser light scattering detector as part of the analysis train. This technique does provide actual molecular weight parameters, but involves costly and time-consuming equipment. In addition, because of the phenomenon being applied, only completely homogeneous homo- or co-polymers can be analyzed. Also, the technique is restricted to the use of solvents which are not inherently highly scattering.

The present invention is straightforward to apply, is not restricted to any particular group of solvents, works for any soluble polymer or copolymer and yields any (or all) molecular weight distribution parameter(s) desired. In addition, the invention results in the measurement of the above-mentioned configuration parameters (Mark-Houwink constants) for the system being examined.

Having now fully described the invention, it will be apparent to one of skill in the art that many obvious modifications and variations exist which do not affect or change the scope thereof.

What is claimed as new and is desired to be secured by Letters Patent is:

1. A method for analyzing a polymer sample, comprising the steps of:
   (a) fractionating the polymer sample by size-exclusion chromatography to produce a stream of polymer solution sorted by polymer molecular size;
   (b) progressively measuring the concentration of said polymer solution stream by means of a mass detector to produce a succession of concentration values and progressively measuring the capillary pressure drop of said polymer solution stream,
   (c) progressively determining the change in viscosity of said polymer solution stream using the change in capillary pressure drop with respect to a known value for the solvent;
   (d) progressively measuring the elution volume of said continuous stream of polymer solution directly, to produce a succession of elution volume values;
   (e) progressively determining the molecular size of the polymer solute as a function of said elution volume values determined by said step (d);
   (f) determining, from said change in viscosity values of step (c), said concentration values of step (b), and said molecular size values of step (e), a molecular weight distribution which describes the polymer sample.

2. The method of claim 1 wherein said mass detector is a differential refractometer.

3. The method of claim 1 wherein said mass detector has a cell volume of less than 20 ul.

4. The method of claim 1 wherein said elution volume values are measured by means of a thermal pulse time-of-flight measurement.

5. The method of claim 1 wherein said mass detector measurements and capillary pressure drop measurements are performed on an eluting stream of polymer solution having an offset volume between said two measurements of less than 50 ul.

6. The method of claim 1 wherein the temperature of the mass detector measurements and capillary pressure drop measurements is controlled to within 0.005° C. or less.

7. The method of claim 1 wherein the mass detector measurements and capillary drop measurements are performed by instruments in close-coupled proximity, and in a thermal sink.

8. The method of claim 1 wherein measurements for specific viscosity and mass are taken at equal intervals of time and are converted to equal intervals of elution volume using additional data calculated by measurement of the actual flow rate through the capillary.

9. The method of claim 1 further including the step of calculation of Mark-Houwink coefficients from said molecular weight distribution data.

10. The method of claim 1 wherein said capillary pressure drop is measured using an input which generates a voltage signal, and comprising the additional step of compensating for the viscosity of the solvent by summing a compensating voltage together with said signal value.

11. The method of claim 1 wherein said capillary pressure drop measurement is effected by means of a differential pressure transducer.

12. The method of claim 11 wherein said differential pressure transducer has a cell volume of less than 20 ul.

13. The method of claim 1 including a pump dampening step.

14. The method of claim 13 wherein said pump dampening step reduces the pump noise to about 0.02% or less.

15. An apparatus for analyzing a polymer sample, comprising:
(a) means for fractionating said polymer sample to produce a continuous stream of polymer solution wherein said polymer is sorted by molecular size;
(b) means for progressively measuring the mass of the polymer solute in said stream;
(c) means for progressively measuring viscosity as a function of change of pressure drop of said polymer solution across a capillary, said means for measuring mass and said means for measuring viscosity being disposed in close-coupled proximity and in a common thermal sink;
(d) means for progressively determining the molecular size of said polymer solution as a function of elution volume; and
(e) means for calculating a molecular weight distribution of the polymer sample using the output from (b), (c) and (d).

16. The apparatus of claim 15 wherein said means for continuously measuring mass is a differential refractometer.

17. The apparatus of claim 15 wherein said mass detector has a cell volume of less than 20 ul.

18. The apparatus of claim 15 wherein said means for measuring molecular size as a function of elution volume comprises a thermal pulse time-of-flight device.

19. The apparatus of claim 15 wherein said means for measuring mass and said means for measuring viscosity are separated by a volume of less than 50 ul.

20. The apparatus of claim 15 wherein said means for measuring mass and said means for measuring viscosity are contained within a thermal sink in a manner such that the temperature of the polymer solution in the means for measuring mass and the polymer solution in the means for measuring viscosity is less than 0.005° C.

21. The apparatus of claim 15 further comprising means for electronically compensating for viscosity across said viscometer due to the solvent therein, such that said differential pressure detector detects the viscosity due to the solute in said solvent alone.

22. The apparatus of claim 15 further comprising apparatus for calculating Mark-Houwink parameters given said values for the molecular weight distribution calculated by said means for calculating molecular weight distribution.

23. The apparatus of claim 15 wherein said means for continuously measuring viscosity as a function of pressure drop across a capillary is a differential pressure transducer.

24. The apparatus of claim 23 wherein said differential pressure transducer has a cell volume of less than 20 ul.

25. The apparatus of claim 15 including a means for dampening pump noise.

26. The apparatus of claim 25 wherein said means for dampening pump noise reduces the pump noise to about 0.02% of the signal generated by the means for measuring viscosity.

27. A method for analyzing a polymer sample in solution, comprising the steps of:
fractionating said polymer sample by size to generate a stream of polymer in solution having molecular sizes varying substantially continuously;
measuring the change in viscosity of the stream of polymer in solution at progressive intervals and storing a series of values thus generated;
determining the concentration of polymer in solution at progressive intervals and storing a series of values thus generated;
compensating said values for the change in viscosity of the solution for the viscosity of the solvent;
dividing the compensated values by those of the corresponding values for concentration to generate a series of values proportional to the intrinsic viscosity of the sample;
progressively measuring the elution volume of the polymer stream and from the elution volume values obtaining the molecular size values of the polymer; and
using the value for the intrinsic viscosity thus derived to calculate the molecular weight of the sample of polymer.

28. The method of claim 27 further including the step of using the molecular weight values and the corresponding intrinsic velocity values to determine the Mark-Houwink coefficients for the polymer-solvent combination and using the derived coefficients and the polymer concentration values to determine the molecular weight distribution which describes the polymer sample.

29. The method of claim 27, wherein the means used to measure the viscosity and the means used to measure polymer concentration are disposed within a controlled thermal sink and are closely coupled.

30. The method of claim 27, wherein one of said series of values is offset with respect to the other to provide compensation for the volume therebetween.

31. The method of claim 27 wherein said step of compensating said values for the change in viscosity of the solution for the viscosity of the solvent in which said polymer sample is dissolved comprises means for compensating values for differential pressure detected across a differential pressure transducer for the pressure drop caused due to the viscosity of said solvent.

32. The method of claim 27 including the step of compensating for volume offset between the series of viscosity values and the series of concentration values by offsetting one series of values with respect to the other.

33. The method of claim 27 comprising the additional step of continuously monitoring the rate of flow of said polymer solution.

34. The method of claim 33 further comprising the step of transforming the values for the viscosity and concentration, measured at regular time intervals, to values for the same variables taken at intervals of constant volume, using said monitored rate of flow.

35. An apparatus, for measuring the molecular weight distribution of the molecules of a polymer sample in solution, comprising:
- means for fractionating the polymer sample according to the molecular size of the molecules of the sample and for eluting the polymer sample in a stream of solvent;
- means for measuring the change in viscosity of the stream of solvent containing the polymer sample at progressive intervals and storing values corresponding thereto;
- means for measuring the mass of the polymer sample in the stream of solvent at progressive intervals and storing values corresponding thereto;
- means for monitoring the elution volume of the stream of solvent containing the polymer sample;
- means for compensating the viscosity values stored in respect to the stream of solvent containing the polymer sample for the contribution to the viscosity due to the solvent;
- means for dividing the compensated viscosity values by corresponding concentration values calculated from the stored mass values in order to generate a sequence of values for the intrinsic viscosity of the polymer sample; and
- means for generating values for the molecular weight distribution of the polymer sample responsive to said means for generating values representing the intrinsic viscosity of the polymer samples.

36. The apparatus of claim 35 further comprising means for conversion of said values for the viscosity and concentration taken at progressive intervals in time to values for the viscosity and the concentration of the polymer sample taken at progressive intervals of elution volume.

37. The apparatus of claim 35, wherein the means for measuring the viscosity of said polymer in solvent outputs a voltage signal, and said means for compensating the values corresponding to the viscosity for the contribution to the viscosity due to the solvent comprises means for summing a compensating voltage with said voltage signals, whereby the portion of said signal due to the viscosity of the solvent is effectively cancelled.

38. The apparatus of claim 35 further comprising means for derivation of Mark-Houwink coefficients from said sequences of values stored with respect to the intrinsic viscosity and molecular weight of the sample.

39. An instrument for determining viscosity and concentration of a stream of polymer samples in solvent, comprising
- a mass detector and a viscosity detector disposed within a single thermal sink in close coupled proximity to one another,
- whereby the composition and temperature of a sample does not change substantially during passage from one of said detectors to the other.

40. The instrument of claim 39, wherein said mass detector is a differential refractometer.

41. The instrument of claim 39, wherein said viscosity detector comprises a capillary and a differential pressure transducer coupled to both ends of said capillary.

42. The instrument of claim 39, wherein said means detector and said viscosity indicator are disposed within a single block of a highly thermally conductive material, whereby their temperatures are maintained at substantially the same level.

* * * * *